(12) United States Patent
Hirata

(10) Patent No.: US 7,252,967 B2
(45) Date of Patent: Aug. 7, 2007

(54) NUCLEIC ACIDS ENCODING CYTOKINE-LIKE PROTEINS THAT PROMOTE CELL PROLIFERATION

(75) Inventor: Yuichi Hirata, Niihari-mura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 526 days.

(21) Appl. No.: 10/440,066

(22) Filed: May 15, 2003

(65) Prior Publication Data

US 2003/0180256 A1    Sep. 25, 2003

Related U.S. Application Data

(60) Division of application No. 09/687,637, filed on Oct. 13, 2000, which is a continuation-in-part of application No. PCT/JP99/01997, filed on Apr. 14, 1999, now Pat. No. 6,610,285.

(30) Foreign Application Priority Data

Apr. 14, 1998    (JP)    ................................. 10/121805

(51) Int. Cl.
*C12P 21/02*    (2006.01)
*C07H 21/04*    (2006.01)
*A61K 38/18*    (2006.01)

(52) U.S. Cl. .................. 435/69.1; 435/69.52; 435/325; 435/252.3; 435/320.1; 536/23.5

(58) Field of Classification Search ..................... None
See application file for complete search history.

(56) References Cited

U.S. PATENT DOCUMENTS 6,060,284 A    5/2000    Bazan ...................... 435/69.52

FOREIGN PATENT DOCUMENTS

WO    WO 00 09552    2/1999
WO    WO 99 05280    2/1999
WO    WO 99/40195    8/1999

OTHER PUBLICATIONS

EMBL Accession No. U38443 dated Jan. 27, 1996.
Prashar et al., "Analysis of Differential Gene Expression by Display of 3' End Restriction Fragments of cDNAs", Proc. Natl. Acad. Science USA. vol. 93, pp. 659-663, 1996.
J. A. Wells. "Additivity of mutational effects in proteins". Biochemistry 29: 8509-8517,1990.
J. T. Ngo et al., "Computational complexity, protein structure prediction. and the Levinthal Paradox", Chapter 14 in The proteinfo. dingproblem and tertiary structure prediction. K. Merz. Jr. Ed.. Birkhauser. Boston. 1994. pp. 492-495.
P. Bork. "Powers and pitfalls in sequence analysis: The 70° hurdle". Genome Research 10: 398-400. 2000.
J. Skolnick et al., "From genes to protein structure and function: novel applications of computational approaches in the genomic era". Trends in Biotech 18(1): 34-39. 2000.
T. Coerks et al., "Protein annotation: detective work for function prediction". Trends in Genetics. 4(g): 248-250. Jun. 1998.
T. F. Smith et al., "The challenges of genome sequence annotation or The devil is in the details". Nature Biotechnology 15: 1222-1223. 1997.
S. E. Brenner. "Errors in genome annotation". Trends in Genetics 15(4)132-133. 1999.
P. Bork. "Go hunting in sequence databases but watch out for the traps". Trends in Genetics 12(10): 425-426. 1996.

*Primary Examiner*—Lorraine M. Spector
(74) *Attorney, Agent, or Firm*—Fish & Richardson P.C.

(57) ABSTRACT

A full-length cDNA corresponding to an EST (AA418955), which does not show any homology to other proteins in the database but has a weak homology to G-CSF, has been successfully isolated by synthesizing printers based on the EST sequence, and effecting PCR-cloning from a human fetal spleen library. Sequencing of the thus-isolated cDNA and analysis of its structure revealed that the cDNA has typical characteristics of a factor belonging to the IL-6/G-CSF/MGF family. It is also found out that the culture supernatant of said sequence-transfected CHO cells shows a proliferation supporting activity towards bone marrow cells in the coexistence of kit ligand.

8 Claims, 12 Drawing Sheets

```
aactcggtga acaactgagg gaaccaaacc agagacgcgc tgaacagaga gaatcaggct 60
caaagcaagt ggaagtgggc agagattcca ccaggactgg tgcaaggcgc agagccagcc 120
agatttgaga agaaggcaaa aag atg ctg ggg agc aga gct gta atg ctg ctg 173
                          Met Leu Gly Ser Arg Ala Val Met Leu Leu
                           1               5                  10 ttg ctg ctg ccc tgg aca gct cag ggc aga gct gtg cct ggg ggc agc   221
Leu Leu Leu Pro Trp Thr Ala Gln Gly Arg Ala Val Pro Gly Gly Ser
                 15                  20                  25 agc cct gcc tgg act cag tgc cag cag ctt tca cag aag ctc tgc aca   269
Ser Pro Ala Trp Thr Gln Cys Gln Gln Leu Ser Gln Lys Leu Cys Thr
             30                  35                  40 ctg gcc tgg agt gca cat cca cta gtg gga cac atg gat cta aga gaa   317
Leu Ala Trp Ser Ala His Pro Leu Val Gly His Met Asp Leu Arg Glu
         45                  50                  55 gag gga gat gaa gag act aca aat gat gtt ccc cat atc cag tgt gga   365
Glu Gly Asp Glu Glu Thr Thr Asn Asp Val Pro His Ile Gln Cys Gly
     60                  65                  70 gat ggc tgt gac ccc caa gga ctc agg gac aac agt cag ttc tgc ttg   413
Asp Gly Cys Asp Pro Gln Gly Leu Arg Asp Asn Ser Gln Phe Cys Leu
 75                  80                  85                  90 caa agg atc cac cag ggt ctg att ttt tat gag aag ctg cta gga tcg   461
Gln Arg Ile His Gln Gly Leu Ile Phe Tyr Glu Lys Leu Leu Gly Ser
                 95                 100                 105 gat att ttc aca ggg gag cct tct ctg ctc cct gat agc cct gtg ggc   509
Asp Ile Phe Thr Gly Glu Pro Ser Leu Leu Pro Asp Ser Pro Val Gly
             110                 115                 120 cag ctt cat gcc tcc cta ctg ggc ctc agc caa ctc ctg cag cct gag   557
Gln Leu His Ala Ser Leu Leu Gly Leu Ser Gln Leu Leu Gln Pro Glu
         125                 130                 135 ggt cac cac tgg gag act cag cag att cca agc ctc agt ccc agc ag   605
Gly His His Trp Glu Thr Gln Gln Ile Pro Ser Leu Ser Pro Ser Gln
     140                 145                 150 cca tgg cag cgt ctc ctt ctc cgc ttc aaa atc ctt cgc agc ctc cag   653
Pro Trp Gln Arg Leu Leu Leu Arg Phe Lys Ile Leu Arg Ser Leu Gln
155                 160                 165                 170 gcc ttt gtg gct gta gcc gcc cgg gtc ttt gcc cat gga gca gca acc   701
Ala Phe Val Ala Val Ala Ala Arg Val Phe Ala His Gly Ala Ala Thr
                 175                 180                 185 ctg agt ccc taaaggcagc agctcaagga tggcactcag atctccatgg           750
Leu Ser Pro
cccagcaagg ccaagataaa tctaccaccc caggcacctg tgagccaaca ggttaattag 810
tccattaatt ttagtgggac ctgcatatgt tgaaaattac caatactgac tgacatgtga 870
tgctgaccta tgataaggtt gagtatttat tagatgggaa gggaaatttg gggattattt 930
atcctcctgg ggacagtttg gggaggatta tttattgtat ttatattgaa ttatgtactt 990
ttttcaataa agtcttattt ttgtggctaa aaaaaa                          1026
```

FIG. 1

FIG. 2 melanoma G361
lung carcinoma A549
colorectal adenocarcinoma SW480
Burkitt's lymphoma Raji
lymphoblastic leukemia MOLT-4
chronic myelogenous leukemia K-562
Hela cell S3
promyelocytic leukemia HL-60

```
tttaaatatttgttctcccttaccoctcccaccccatcccgctgtgccccccatcccgccccttctatagctatttcgattcctgsagagcattacac  100 atgtgtcccatcccaggcctctagccacagcagccacactactcatttccctggaactgaggctgcataccctgggctccccacagagggggatgatgca  200
                                TATA
gggagggganteccacctgctgtgagtcacctgctggtataagggcgggccttacaatgcagggaccttaaaagactcagagacaaagggagaaaaaca  300 acaggaagcagcttacaAACTCGGTGAACAACTGAGGGAACCAAACCAGAGACGCGCTGAACAGAGAGAATCAGGCTCAAAGCAAGTGGAAGTGGGCAGA  400

GATTCCACCAGGACTGGTGCAAGGCGCAGAGCCAGCCAGATTTGAGAAGAAGGCAAAAAGATGCTGGGGAGCAGAGCTGTAATGCTGCTGTTGCTGCTGC  500
                                                           M  L  G  S  R  A  V  M  L  L  L  L  P
                                                          -19                          -10
CCTGGACAGCTCAGGGCAGAGCTGTGCCTGGGGGCAGCAGCCCTGCCTGGACTCAGTGCCAGCAGCTTTCACAGAAGCTCTGCACACTGGCCTGGAGTGC  600
  W  T  A  Q  G  R  A  V  P  G  G  S  S  P  A  W  T  Q  C  Q  Q  L  S  Q  K  L  C  T  L  A  W  S  A
                  1                          10                         20
ACATCCACTAGTGGGACACATGgtgagtggcagccctggagcctaacaggagtccaggctctccaaggctgtggcagaagaccgtgaccttgagtggaa  700
  H  P  L  V  G  H  M
                 30
gctggagggttgaaggccattaggagtaagagaggacaagagagtgggttcctgggagagtcatgggcctgagggtccaggttggcttcagaagtact  800 atcttacttcttcattctttccacctcttccttcattccagGATCTAAGAGAAGAGGGGAGATGAAGAGACTACAAATGATGTTCCCCATATCCAGTGTGG  900
                                         D  L  R  E  E  G  D  E  E  T  T  N  D  V  P  H  I  Q  C  G
                                            40                         50
AGATGGCTGTGACCCCCAAGGACTCAGGGACAACAGTCAGgtaccactgggatgtggctgggcaatgaaggagaggggactgagaacatggctgggtacc  1000
  D  G  C  D  P  Q  G  L  R  D  N  S  Q
                       60
atggtaaaccagaagttgtgtctgaaaatagtaagaaactgggtgagtcttcagtgaatggagtaggaagagggtgtcctctttcattgctttctttct  1100 ccctagTTCTGCTTGCAAAGGATCCACCAGGGTCTGATTTTTTATGAGAAGCTGCTAGGATCGGATATTTCACAGGGGAGCCTTCTCTGCTCCCTGATA  1200
      F  C  L  Q  R  I  H  Q  G  L  I  F  Y  E  K  L  L  G  S  D  I  F  T  G  E  P  S  L  L  P  D  S
      70                         80                         90                         100
GCCCTGTGGGCCAGCTTCATGCCTCCCTACTGGGCCTCAGCCAACTCCTGCAGgtatgaagtagggcgtggaggatggggcttgcaggtgtcagagac  1300
  P  V  G  Q  L  H  A  S  L  L  G  L  S  Q  L  L  Q
                     110
agaggcttgggggttaagggtttagagtcttctctgactgtgtcctatgtccttcagCCTGAGGGTCACCACTGGGAGACTCAGCAGATTCCAAGCCTC  1400
                                                         P  E  G  H  H  W  E  T  Q  Q  I  P  S  L
                                                                     120                    130
AGTCCAGCCAGCCATGGCAGCGTCTCCTTCTCCGCTTCAAAATCCTTCGCAGCCTCCAGGCCTTTGTGGCTGTAGCCGCCCGGGTCTTTGCCCATGGAG  1500
  S  P  S  Q  P  W  Q  R  L  L  L  R  F  K  I  L  R  S  L  Q  A  F  V  A  V  A  A  R  V  F  A  H  G  A
                      140                        150                        160
CAGCAACCCTGAGTCCCTAAAGGCAGCAGCTCAAGGATGGCACTCAGATCTCCATGGCCCAGCAAGGCCAAGATAAATCTACCACCCCAGGCACCTGTGA  1600
  A  T  L  S  P  *
           170
GCCAACAGGTTAATTAGTCCATTAATTTTTAGTGGGACCTGCATATGTTGAAAATTACCAATACTGACTGACATGTGATGCTGACCTATGATAAGGTTGAG  1700

TATTTATTAGATGGGAAGGGAAATTTGGGGATTATTTATCCTCCTGGGGACAGTTTGGGGAGGATTATTTATTGTATTTATATTGAATTATGTACTTTTT  1800
                                                                polyA
TCAATAAAGTCTTATTTTTGTGGCTAtatgagtctaattctaggctcaattgggaaagagaaatcgatggaaaaataaggccaagagactacaatatgc  1900 atcccttcttctatctgaagggctatggtggagaatgatattttctcatgacccctggtgtatagaataactgggatctctttagtattaattccta  2000 tatggctgagcaagcagaatgggattaccagattaggaagtgggatcatacctaagggtcaactgctccctgatccagtgtctccttccctgcttcttg  2100 gccaagagtatatctgatcaaagacgggagtcctgatcattgcaggetcaaagtcagagttcagctttgagcagguagcgcattccagggauatgaaga  2200 taaatatcctagaataatgggacttccttctcaaaggucaattggaatccctttttttttttttttttttttttttttttttgagatggagtctcattct  2300 gttgcccaggctggagtgcagtggcgtgutctctgctcactgcaacctccgcctcccacgttgaagcgattctcctgcctcagcctcccaagcagctg  2398
```

*pLG-SGRFg*

- H-2Ld
- PvuII
- SphI
- BamHI
- Rbt β globin
- EcoRI
- SGRF genomic DNA
- BamHI
- 4 X ARE
- SGRF poly A
- XhoI
- SV40 poly A
- Ori
- Amp^r

SEQUENCE LISTING

<160> NUMBER OF SEQ ID NOS: 46
<210> SEQ ID NO 1
<211> LENGTH: 189
<212> TYPE: PRT
<213> ORGANISM: Homo sapiens

<400> SEQUENCE: 1

Met Leu Gly Ser Arg Ala Val Met Leu Leu Leu Leu Pro Trp Thr
 1               5                  10                  15

Ala Gln Gly Arg Ala Val Pro Gly Gly Ser Ser Pro Ala Trp Thr Gln
                20                  25                  30

Cys Gln Gln Leu Ser Gln Lys Leu Cys Thr Leu Ala Trp Ser Ala His
                35                  40                  45

Pro Leu Val Gly His Met Asp Leu Arg Glu Glu Gly Asp Glu Glu Thr
        50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
                100                 105                 110

Pro Ser Leu Leu Pro Asp Ser Pro Val Gly Gln Leu His Ala Ser Leu
                115                 120                 125

```
Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 2
<211> LENGTH: 1026
<212> TYPE: DNA
<213> ORGANISM: Homo sapiens
<220> FEATURE:
<221> NAME/KEY: CDS
<222> LOCATION: (144)...(710)

<400> SEQUENCE: 2
aactcggtga caactgagg gaaccaaacc agagacgcgc tgaacagaga gaatcaggct      60
caaagcaagt ggaagtgggc agagattcca ccaggactgg tgcaaggcgc agagccagcc   120
agatttgaga agaaggcaaa aag atg ctg ggg agc aga gct gta atg ctg ctg   173
                         Met Leu Gly Ser Arg Ala Val Met Leu Leu
                           1               5                  10 ttg ctg ctg ccc tgg aca gct cag ggc aga gct gtg cct ggg ggc agc     221
Leu Leu Leu Pro Trp Thr Ala Gln Gly Arg Ala Val Pro Gly Gly Ser
                15                  20                  25 agc cct gcc tgg act cag tgc cag cag ctt tca cag aag ctc tgc aca     269
Ser Pro Ala Trp Thr Gln Cys Gln Gln Leu Ser Gln Lys Leu Cys Thr
        30                  35                  40 ctg gcc tgg agt gca cat cca cta gtg gga cac atg gat cta aga gaa     317
Leu Ala Trp Ser Ala His Pro Leu Val Gly His Met Asp Leu Arg Glu
    45                  50                  55 gag gga gat gaa gag act aca aat gat gtt ccc cat atc cag tgt gga     365
Glu Gly Asp Glu Glu Thr Thr Asn Asp Val Pro His Ile Gln Cys Gly
60                  65                  70 gat ggc tgt gac ccc caa gga ctc agg gac aac agt cag ttc tgc ttg     413
Asp Gly Cys Asp Pro Gln Gly Leu Arg Asp Asn Ser Gln Phe Cys Leu
75                  80                  85                  90 caa agg atc cac cag ggt ctg att ttt tat gag aag ctg cta gga tcg     461
Gln Arg Ile His Gln Gly Leu Ile Phe Tyr Glu Lys Leu Leu Gly Ser
                95                 100                 105 gat att ttc aca ggg gag cct tct ctg ctc cct gat agc cct gtg ggc     509
Asp Ile Phe Thr Gly Glu Pro Ser Leu Leu Pro Asp Ser Pro Val Gly
            110                 115                 120 cag ctt cat gcc tcc cta ctg ggc ctc agc caa ctc ctg cag cct gag     557
Gln Leu His Ala Ser Leu Leu Gly Leu Ser Gln Leu Leu Gln Pro Glu
        125                 130                 135 ggt cac cac tgg gag act cag cag att cca agc ctc agt ccc agc cag     605
Gly His His Trp Glu Thr Gln Gln Ile Pro Ser Leu Ser Pro Ser Gln
    140                 145                 150 cca tgg cag cgt ctc ctt ctc cgc ttc aaa atc ctt cgc agc ctc cag     653
Pro Trp Gln Arg Leu Leu Leu Arg Phe Lys Ile Leu Arg Ser Leu Gln
155                 160                 165                 170 gcc ttt gtg gct gta gcc gcc cgg gtc ttt gcc cat gga gca gca acc     701
Ala Phe Val Ala Val Ala Ala Arg Val Phe Ala His Gly Ala Ala Thr
                175                 180                 185 ctg agt ccc taaggcagc agctcaagga tggcactcag atctccatgg              750
Leu Ser Pro cccagcaagg ccaagataaa tctaccaccc caggcacctg tgagccaaca ggttaattag   810
```

```
tccattaatt ttagtgggac ctgcatatgt tgaaaattac caatactgac tgacatgtga    870
tgctgaccta tgataaggtt gagtatttat tagatgggaa gggaaatttg gggattattt    930
atcctcctgg ggacagtttg gggaggatta tttattgtat ttatattgaa ttatgtactt    990
ttttcaataa agtcttattt ttgtggctaa aaaaaa                             1026
```

<210> SEQ ID NO 3
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 3

```
gagaagaggg agatgaagag actac                                           25
```

<210> SEQ ID NO 4
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 4

```
ctgagtcctt gggggtcaca gccat                                           25
```

<210> SEQ ID NO 5
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 5

```
gtgggacctg catatgttga aaatt                                           25
```

<210> SEQ ID NO 6
<211> LENGTH: 26
<212> TYPE: DNA
<213> ORGANISM: Artificial Sequence
<220> FEATURE:
<223> OTHER INFORMATION: Artificially synthesized primer sequence

<400> SEQUENCE: 6

```
ccccaaattt cccttcccat ctaata                                          26
```

<210> SEQ ID NO 7
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 7

```
ccctactggg cctcagccaa ctcct                                           25
```

<210> SEQ ID NO 8
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 8

```
ggagcagaga aggctcccct gtgaa                                           25

<210> SEQ ID NO 9
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 9
gggcagagat tccaccagga ctggt                                           25

<210> SEQ ID NO 10
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 10
ccagtcctgg tggaatctct gccca                                           25

<210> SEQ ID NO 11
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 11
gaagctctgc acactggcct ggagt                                           25

<210> SEQ ID NO 12
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 12
cactccaggc cagtgtgcag agctt                                           25

<210> SEQ ID NO 13
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 13
ctgaagggct atggtggaga a                                               21

<210> SEQ ID NO 14
<211> LENGTH: 32
<212> TYPE: DNA
<213> ORGANISM: Artificial Sequence
<220> FEATURE:
<223> OTHER INFORMATION: Artificially synthesized primer sequence

<400> SEQUENCE: 14
ttgaattcca ccatgctggg gagcagagct gt                                   32

<210> SEQ ID NO 15
<211> LENGTH: 28
<212> TYPE: DNA
<213> ORGANISM: Artificial Sequence
```

```
<220> FEATURE:
<223> OTHER INFORMATION: Artificially synthesized primer sequence

<400> SEQUENCE: 15
aaagatctta gggactcagg gttgctgc                                      28

<210> SEQ ID NO 16
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 16
aagaattcta gggactcagg gttgctgc                                      28

<210> SEQ ID NO 17
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 17
ggtttaaata tttgttctcc cttacccc                                      28

<210> SEQ ID NO 18
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 18
ttcagctgct tgggaggctg aggcagg                                       27

<210> SEQ ID NO 19
<211> LENGTH: 31
<212> TYPE: DNA
<213> ORGANISM: Artificial Sequence
<220> FEATURE:
<223> OTHER INFORMATION: Artificially synthesized primer sequence

<400> SEQUENCE: 19
aggaattcca ccaggactgg tgcaaggcgc a                                  31

<210> SEQ ID NO 20
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 20
gtctcgagaa aatatcattc tccaccatag ccct                               34

<210> SEQ ID NO 21
<211> LENGTH: 2398
<212> TYPE: DNA
<213> ORGANISM: Homo sapiens
<220> FEATURE:
<221> NAME/KEY: CDS
<222> LOCATION: (461)...(622)
<220> FEATURE:
<221> NAME/KEY: CDS
<222> LOCATION: (842)...(940)
<220> FEATURE:
```

```
<221> NAME/KEY: CDS
<222> LOCATION: (1107)...(1253)
<220> FEATURE:
<221> NAME/KEY: CDS
<222> LOCATION: (1359)...(1517)
<220> FEATURE:
<221> NAME/KEY: exon
<222> LOCATION: (318)...(622)
<220> FEATURE:
<221> NAME/KEY: intron
<222> LOCATION: (623)...(841)
<220> FEATURE:
<221> NAME/KEY: exon
<222> LOCATION: (842)...(940)
<220> FEATURE:
<221> NAME/KEY: intron
<222> LOCATION: (941)...(1106)
<220> FEATURE:
<221> NAME/KEY: exon
<222> LOCATION: (1107)...(1253)
<220> FEATURE:
<221> NAME/KEY: intron
<222> LOCATION: (1254)...(1358)
<220> FEATURE:
<221> NAME/KEY: exon
<222> LOCATION: (1359)...(1826)
<220> FEATURE:
<221> NAME/KEY: TATA_signal
<222> LOCATION: (238)...(242)
<220> FEATURE:
<221> NAME/KEY: polyA_signal
<222> LOCATION: (1803)...(1807)

<400> SEQUENCE: 21
```

| | |
|---|---|
| tttaaatatt tgttctccct taccccctccc acccccatccc cgctgtgccc cccatccccg | 60 |
| cccccttctat agctatttcg attcctggag agcattacac atgtgtccca tcccaggcct | 120 |
| ctagccacag caaccacact actcatttcc cctggaactg aggctgcata cctgggctcc | 180 |
| ccacagaggg ggatgatgca gggaggggaa tcccacctgc tgtgagtcac ctgctggtat | 240 |
| aaaggggcggg ccttacaatg cagggacctt aaaagactca gagacaaagg gagaaaaaca | 300 |
| acaggaagca gcttacaaac tcggtgaaca actgagggaa ccaaaccaga gacgcgctga | 360 |
| acagagagaa tcaggctcaa agcaagtgga agtgggcaga gattccacca ggactggtgc | 420 |
| aaggcgcaga gccagccaga tttgagaaga aggcaaaaag atg ctg ggg agc aga<br>                                                                                Met Leu Gly Ser Arg<br>                                                                                 1              5 | 475 |
| gct gta atg ctg ctg ttg ctg ctg ccc tgg aca gct cag ggc aga gct<br>Ala Val Met Leu Leu Leu Leu Leu Pro Trp Thr Ala Gln Gly Arg Ala<br>                10                       15                       20 | 523 |
| gtg cct ggg ggc agc agc cct gcc tgg act cag tgc cag cag ctt tca<br>Val Pro Gly Gly Ser Ser Pro Ala Trp Thr Gln Cys Gln Gln Leu Ser<br>                     25                       30                       35 | 571 |
| cag aag ctc tgc aca ctg gcc tgg agt gca cat cca cta gtg gga cac<br>Gln Lys Leu Cys Thr Leu Ala Trp Ser Ala His Pro Leu Val Gly His<br> 40                       45                       50 | 619 |
| atg gtgagtggca gcccctggag cctaacagga gtccaggctc tccaaggctg<br>Met | 672 |
| tggcagaaga ccgtgacctt gagtggaagc tggagggttg aaggccatta gggagtaaga | 732 |
| gaggacaaga gagtagggtt cctgggagag tcatgggcct gagggtccag gttggcttca | 792 |
| gaagtactat cttacttctt cattctttcc acctcttcct tcattccag gat cta aga<br>                                                                                  Asp Leu Arg<br>                                                                                                           55 | 850 |
| gaa gag gga gat gaa gag act aca aat gat gtt ccc cat atc cag tgt<br>Glu Glu Gly Asp Glu Glu Thr Thr Asn Asp Val Pro His Ile Gln Cys<br> 60                       65                       70 | 898 |

```
gga gat ggc tgt gac ccc caa gga ctc agg gac aac agt cag        940
Gly Asp Gly Cys Asp Pro Gln Gly Leu Arg Asp Asn Ser Gln
         75                  80                  85 gtaccactgg gatgtggctg gcaatgaag gagaggggac tgagaacatg gctgggtacc   1000
atggtaaacc agaagttgtg tctgaaaata gtaagaaact gggtgagtct tcagtgaatg  1060
gagtaggaag agggtgtcct ctttcattgc tttcttttct ccctag ttc tgc ttg    1115
                                                  Phe Cys Leu
                                                            90 caa agg atc cac cag ggt ctg att ttt tat gag aag ctg cta gga tcg   1163
Gln Arg Ile His Gln Gly Leu Ile Phe Tyr Glu Lys Leu Leu Gly Ser
         95                 100                 105 gat att ttc aca ggg gag cct tct ctg ctc cct gat agc cct gtg ggc   1211
Asp Ile Phe Thr Gly Glu Pro Ser Leu Leu Pro Asp Ser Pro Val Gly
        110                 115                 120 cag ctt cat gcc tcc cta ctg ggc ctc agc caa ctc ctg cag           1253
Gln Leu His Ala Ser Leu Leu Gly Leu Ser Gln Leu Leu Gln
        125                 130                 135 gtatgaagta gggcgtgga ggatgggggc ttgcaggtgt cagagacaga gggttggggg   1313
ttaagggttt agagtcttct ctgactgtgt cctatgtcct ttcag cct gag ggt cac 1370
                                                  Pro Glu Gly His
                                                              140 cac tgg gag act cag cag att cca agc ctc agt ccc agc cag cca tgg   1418
His Trp Glu Thr Gln Gln Ile Pro Ser Leu Ser Pro Ser Gln Pro Trp
            145                 150                 155 cag cgt ctc ctt ctc cgc ttc aaa atc ctt cgc agc ctc cag gcc ttt   1466
Gln Arg Leu Leu Leu Arg Phe Lys Ile Leu Arg Ser Leu Gln Ala Phe
        160                 165                 170 gtg gct gta gcc gcc cgg gtc ttt gcc cat gga gca gca acc ctg agt   1514
Val Ala Val Ala Ala Arg Val Phe Ala His Gly Ala Ala Thr Leu Ser
        175                 180                 185 ccc taaaggcagc agctcaagga tggcactcag atctccatgg cccagcaagg        1567
Pro ccaagataaa tctaccaccc caggcacctg tgagccaaca ggttaattag tccattaatt  1627
ttagtgggac ctgcatatgt tgaaaattac caatactgac tgacatgtga tgctgaccta  1687
tgataaggtt gagtatttat tagatgggaa gggaaatttg gggattattt atcctcctgg  1747
ggacagtttg gggaggatta tttattgtat ttatattgaa ttatgtactt ttttcaataa  1807
agtcttattt ttgtggctat atgagtctaa tttctaggct caattgggaa agagaaatcg  1867
atggaaaaat aaggccaaga gactacaata tgcatccctt tcttctattc tgaagggcta  1927
tggtggagaa tgatattttc tcatgacccc ctggtgtata gaataactgg gatctcttta  1987
gtattaattc ctatatggct gagcaagcag aatgggatta ccagattagg aagtgggatc  2047
atacctaagg gtcacttgct ccctgatcca gtgtctcctt ccctgctttc ttggccaaga  2107
gtatatctga tcaaagacgg gagtcctgat cattgcagga tcaaaagtca gagttcagct  2167
ttgagcagga agggcattcc agggaaatga agataaatat cctagaataa tgggactttc  2227
ctctcaaagg acaattggaa tcccttttt tttttttttt tttttttttt ttttttgagat  2287 ggagtctcat tctgttgccc aggctggagt gcagtggcgt gatctctgct cactgcaacc  2347
tccgcctccc acgttgaagc gattctcctg cctcagcctc ccaagcagct g          2398

<210> SEQ ID NO 22
<211> LENGTH: 54
<212> TYPE: PRT
<213> ORGANISM: Homo sapiens
```

<400> SEQUENCE: 22

Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
                20                  25                  30

Cys Gln Gln Leu Ser Gln Lys Leu Cys Thr Leu Ala Trp Ser Ala His
                35                  40                  45

Pro Leu Val Gly His Met
        50

<210> SEQ ID NO 23
<211> LENGTH: 33
<212> TYPE: PRT
<213> ORGANISM: Homo sapiens

<400> SEQUENCE: 23

Asp Leu Arg Glu Glu Gly Asp Glu Glu Thr Thr Asn Asp Val Pro His
1               5                   10                  15

Ile Gln Cys Gly Asp Gly Cys Asp Pro Gln Gly Leu Arg Asp Asn Ser
                20                  25                  30

Gln

<210> SEQ ID NO 24
<211> LENGTH: 49
<212> TYPE: PRT
<213> ORGANISM: Homo sapiens

<400> SEQUENCE: 24

Phe Cys Leu Gln Arg Ile His Gln Gly Leu Ile Phe Tyr Glu Lys Leu
1               5                   10                  15

Leu Gly Ser Asp Ile Phe Thr Gly Glu Pro Ser Leu Leu Pro Asp Ser
                20                  25                  30

Pro Val Gly Gln Leu His Ala Ser Leu Leu Gly Leu Ser Gln Leu Leu
        35                  40                  45

Gln

<210> SEQ ID NO 25
<211> LENGTH: 53
<212> TYPE: PRT
<213> ORGANISM: Homo sapiens

<400> SEQUENCE: 25

Pro Glu Gly His His Trp Glu Thr Gln Gln Ile Pro Ser Leu Ser Pro
1               5                   10                  15

Ser Gln Pro Trp Gln Arg Leu Leu Leu Arg Phe Lys Ile Leu Arg Ser
                20                  25                  30

Leu Gln Ala Phe Val Ala Val Ala Ala Arg Val Phe Ala His Gly Ala
        35                  40                  45

Ala Thr Leu Ser Pro
    50

<210> SEQ ID NO 26
<211> LENGTH: 26
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT

```
<222> LOCATION: 2-10, 12-17, 20-21, 23-25
<223> OTHER INFORMATION: Xaa = any amino acid
<220> FEATURE:
<221> NAME/KEY: VARIANT
<222> LOCATION: 22
<223> OTHER INFORMATION: Xaa = Phe, or Tyr

<400> SEQUENCE: 26

Cys Xaa Xaa Xaa Xaa Xaa Xaa Xaa Xaa Cys Xaa Xaa Xaa Xaa
 1               5                  10                  15

Xaa Gly Leu Xaa Xaa Xaa Xaa Xaa Xaa Leu
            20                  25

<210> SEQ ID NO 27
<211> LENGTH: 7
<212> TYPE: PRT
<213> ORGANISM: Homo sapiens
<220> FEATURE:
<221> NAME/KEY: UNSURE
<222> LOCATION: (1)
<223> OTHER INFORMATION: Xaa = unsure

<400> SEQUENCE: 27

Xaa Ala Val Pro Gly Gly Ser
 1               5

<210> SEQ ID NO 28
<211> LENGTH: 55
<212> TYPE: PRT
<213> ORGANISM: Mustela vison

<400> SEQUENCE: 28

Ala Glu Asn Asn Leu Lys Leu Pro Lys Leu Ala Glu Lys Asp Lys Cys
 1               5                  10                  15

Phe Gln Ser Gln Phe Asn Gln Glu Thr Cys Met Thr Arg Ile Thr Thr
            20                  25                  30

Gly Leu Gln Glu Phe Gln Ile His Leu Lys Tyr Leu Gly Ala Asn Tyr
        35                  40                  45

Glu Gly Asn Lys Asn Asn Ala
    50                  55

<210> SEQ ID NO 29
<211> LENGTH: 89
<212> TYPE: PRT
<213> ORGANISM: Capra hircus

<400> SEQUENCE: 29

Lys Thr Glu Ala Leu Ile Lys His Ile Val Asp Lys Ile Ser Ala Ile
 1               5                  10                  15

Arg Lys Glu Ile Cys Glu Lys Asn Asp Glu Cys Glu Asn Ser Lys Glu
            20                  25                  30

Thr Leu Ala Glu Asn Lys Leu Lys Leu Pro Lys Met Glu Glu Lys Asp
        35                  40                  45

Gly Cys Phe Gln Ser Gly Phe Asn Gln Ala Ile Cys Leu Ile Lys Thr
    50                  55                  60

Thr Ala Gly Leu Leu Glu Tyr Gln Ile Tyr Leu Asp Phe Leu Gln Asn
65                  70                  75                  80

Glu Phe Glu Gly Asn Gln Glu Thr Val
                85

<210> SEQ ID NO 30
<211> LENGTH: 89
```

```
<212> TYPE: PRT
<213> ORGANISM: Ovis aries

<400> SEQUENCE: 30

Lys Thr Glu Ala Leu Ile Lys His Ile Val Asp Lys Ile Ser Ala Ile
 1               5                  10                  15

Arg Lys Glu Ile Cys Glu Lys Asn Asp Glu Cys Glu Asn Ser Lys Glu
             20                  25                  30

Thr Leu Ala Glu Asn Lys Leu Lys Leu Pro Lys Met Glu Glu Lys Asp
         35                  40                  45

Gly Cys Phe Gln Ser Gly Phe Asn Gln Ala Ile Cys Leu Ile Lys Thr
     50                  55                  60

Thr Ala Gly Leu Leu Glu Tyr Gln Ile Tyr Leu Asp Phe Leu Gln Asn
 65                  70                  75                  80

Glu Phe Glu Gly Asn Gln Glu Thr Val
                 85

<210> SEQ ID NO 31
<211> LENGTH: 89
<212> TYPE: PRT
<213> ORGANISM: Bos taurus

<400> SEQUENCE: 31

Lys Thr Glu Ala Leu Ile Lys Arg Met Val Asp Lys Ile Ser Ala Met
 1               5                  10                  15

Arg Lys Glu Ile Cys Glu Lys Asn Asp Glu Cys Glu Ser Ser Lys Glu
             20                  25                  30

Thr Leu Ala Glu Asn Lys Leu Asn Leu Pro Lys Met Glu Glu Lys Asp
         35                  40                  45

Gly Cys Phe Gln Ser Gly Phe Asn Gln Ala Ile Cys Leu Ile Arg Thr
     50                  55                  60

Thr Ala Gly Leu Leu Glu Tyr Gln Ile Tyr Leu Asp Tyr Leu Gln Asn
 65                  70                  75                  80

Glu Tyr Glu Gly Asn Gln Glu Asn Val
                 85

<210> SEQ ID NO 32
<211> LENGTH: 89
<212> TYPE: PRT
<213> ORGANISM: Equus caballus

<400> SEQUENCE: 32

Lys Thr Lys Gln His Ile Lys Tyr Ile Leu Gly Lys Ile Ser Ala Leu
 1               5                  10                  15

Lys Asn Glu Met Cys Asn Asn Phe Ser Lys Cys Glu Asn Ser Lys Glu
             20                  25                  30

Val Leu Ala Glu Asn Asn Leu Asn Leu Pro Lys Met Ala Glu Lys Asp
         35                  40                  45

Gly Cys Phe Gln Ser Gly Phe Asn Gln Glu Thr Cys Leu Met Lys Ile
     50                  55                  60

Thr Thr Gly Leu Ser Glu Phe Gln Ile Tyr Leu Glu Tyr Leu Gln Asn
 65                  70                  75                  80

Glu Phe Lys Gly Glu Lys Glu Asn Ile
                 85

<210> SEQ ID NO 33
<211> LENGTH: 89
<212> TYPE: PRT
```

-continued

<213> ORGANISM: Sus scrofa

<400> SEQUENCE: 33

Lys Thr Glu Glu Leu Ile Lys Tyr Ile Leu Gly Lys Ile Ser Ala Met
1               5                   10                  15

Arg Lys Glu Met Cys Glu Lys Tyr Glu Lys Cys Glu Asn Ser Lys Glu
            20                  25                  30

Val Leu Ala Glu Asn Asn Leu Asn Leu Pro Lys Met Ala Glu Lys Asp
        35                  40                  45

Gly Cys Phe Gln Ser Gly Phe Asn Gln Glu Thr Cys Leu Met Arg Ile
    50                  55                  60

Thr Thr Gly Leu Val Glu Phe Gln Ile Tyr Leu Asp Tyr Leu Gln Lys
65                  70                  75                  80

Glu Tyr Glu Ser Asn Lys Gly Asn Val
                85

<210> SEQ ID NO 34
<211> LENGTH: 89
<212> TYPE: PRT
<213> ORGANISM: Canis familiaris

<400> SEQUENCE: 34

Lys Val Glu Glu Leu Ile Lys Tyr Ile Leu Gly Lys Ile Ser Ala Leu
1               5                   10                  15

Arg Lys Glu Met Cys Asp Lys Phe Asn Lys Cys Glu Asp Ser Lys Glu
            20                  25                  30

Ala Leu Ala Glu Asn Asn Leu His Leu Pro Lys Leu Glu Gly Lys Asp
        35                  40                  45

Gly Cys Phe Gln Ser Gly Phe Asn Gln Glu Thr Cys Leu Thr Arg Ile
    50                  55                  60

Thr Thr Gly Leu Val Glu Phe Gln Leu His Leu Asn Ile Leu Gln Asn
65                  70                  75                  80

Asn Tyr Glu Gly Asp Lys Glu Asn Val
                85

<210> SEQ ID NO 35
<211> LENGTH: 89
<212> TYPE: PRT
<213> ORGANISM: Felis catus

<400> SEQUENCE: 35

Lys Met Glu Glu Leu Ile Lys Tyr Ile Leu Gly Lys Ile Ser Ala Leu
1               5                   10                  15

Lys Lys Glu Met Cys Asp Asn Tyr Asn Lys Cys Glu Asp Ser Lys Glu
            20                  25                  30

Ala Leu Ala Glu Asn Asn Leu Asn Leu Pro Lys Leu Ala Glu Lys Asp
        35                  40                  45

Gly Cys Phe Gln Ser Gly Phe Asn Gln Glu Thr Cys Leu Thr Arg Ile
    50                  55                  60

Thr Thr Gly Leu Gln Glu Phe Gln Ile Tyr Leu Lys Phe Leu Gln Asp
65                  70                  75                  80

Lys Tyr Glu Gly Asp Glu Glu Asn Ala
                85

<210> SEQ ID NO 36
<211> LENGTH: 89
<212> TYPE: PRT
<213> ORGANISM: Cercocebus torquatus atys

<400> SEQUENCE: 36

Arg Ile Asp Lys His Ile Arg Tyr Ile Leu Asp Gly Ile Ser Ala Leu
1               5                   10                  15

Arg Lys Glu Thr Cys Asn Arg Ser Asn Met Cys Asp Ser Thr Lys Glu
            20                  25                  30

Ala Leu Ala Glu Asn Asn Leu Asn Leu Pro Lys Met Ala Glu Lys Asp
        35                  40                  45

Gly Cys Phe Gln Ser Gly Phe Asn Glu Asp Thr Cys Leu Val Lys Ile
    50                  55                  60

Ile Thr Gly Leu Leu Glu Phe Glu Val Tyr Leu Glu Tyr Leu Gln Asn
65                  70                  75                  80

Arg Phe Glu Ser Ser Glu Glu Gln Ala
                85

<210> SEQ ID NO 37
<211> LENGTH: 89
<212> TYPE: PRT
<213> ORGANISM: Macaca mulatta

<400> SEQUENCE: 37

Arg Ile Asp Lys His Ile Arg Tyr Ile Leu Asp Gly Ile Ser Ala Leu
1               5                   10                  15

Arg Lys Glu Thr Cys Asn Arg Ser Asn Met Cys Glu Ser Ser Lys Glu
            20                  25                  30

Ala Leu Ala Glu Asn Asn Leu Asn Leu Pro Lys Met Ala Glu Lys Asp
        35                  40                  45

Gly Cys Phe Gln Ser Gly Phe Asn Glu Asp Thr Cys Leu Val Lys Ile
    50                  55                  60

Ile Thr Gly Leu Leu Glu Phe Glu Val Tyr Leu Glu Tyr Leu Gln Asn
65                  70                  75                  80

Arg Phe Glu Ser Ser Glu Glu Gln Ala
                85

<210> SEQ ID NO 38
<211> LENGTH: 89
<212> TYPE: PRT
<213> ORGANISM: Homo sapiens

<400> SEQUENCE: 38

Arg Ile Asp Lys Gln Ile Arg Tyr Ile Leu Asp Gly Ile Ser Ala Leu
1               5                   10                  15

Arg Lys Glu Thr Cys Asn Lys Ser Asn Met Cys Glu Ser Ser Lys Glu
            20                  25                  30

Ala Leu Ala Glu Asn Asn Leu Asn Leu Pro Lys Met Ala Glu Lys Asp
        35                  40                  45

Gly Cys Phe Gln Ser Gly Phe Asn Glu Glu Thr Cys Leu Val Lys Ile
    50                  55                  60

Ile Thr Gly Leu Leu Glu Phe Glu Val Tyr Leu Glu Tyr Leu Gln Asn
65                  70                  75                  80

Arg Phe Glu Ser Ser Glu Glu Gln Ala
                85

<210> SEQ ID NO 39
<211> LENGTH: 89
<212> TYPE: PRT
<213> ORGANISM: Mus musculus -continued

<400> SEQUENCE: 39

Gln Val Gly Gly Leu Ile Thr His Val Leu Trp Glu Ile Val Glu Met
1               5                   10                  15

Arg Lys Glu Leu Cys Asn Gly Asn Ser Asp Cys Met Asn Asn Asp Asp
            20                  25                  30

Ala Leu Ala Glu Asn Asn Leu Lys Leu Pro Glu Ile Gln Arg Asn Asp
        35                  40                  45

Gly Cys Tyr Gln Thr Gly Tyr Asn Gln Glu Ile Cys Leu Leu Lys Ile
    50                  55                  60

Ser Ser Gly Leu Leu Glu Tyr His Ser Tyr Leu Glu Tyr Met Lys Asn
65                  70                  75                  80

Asn Leu Lys Asp Asn Lys Lys Asp Lys
                85

<210> SEQ ID NO 40
<211> LENGTH: 89
<212> TYPE: PRT
<213> ORGANISM: Rattus norvegicus

<400> SEQUENCE: 40

Gln Val Gly Gly Leu Ile Thr Tyr Val Leu Arg Glu Ile Leu Glu Met
1               5                   10                  15

Arg Lys Glu Leu Cys Asn Gly Asn Ser Asp Cys Met Asn Ser Asp Asp
            20                  25                  30

Ala Leu Ser Glu Asn Asn Leu Lys Leu Pro Glu Ile Gln Arg Asn Asp
        35                  40                  45

Gly Cys Phe Gln Thr Gly Tyr Asn Gln Glu Ile Cys Leu Leu Lys Ile
    50                  55                  60

Cys Ser Gly Leu Leu Glu Phe Arg Phe Tyr Leu Glu Phe Val Lys Asn
65                  70                  75                  80

Asn Leu Gln Asp Asn Lys Lys Asp Lys
                85

<210> SEQ ID NO 41
<211> LENGTH: 88
<212> TYPE: PRT
<213> ORGANISM: Bos taurus

<400> SEQUENCE: 41

Lys Cys Leu Glu Gln Val Arg Lys Ile Gln Ala Asp Gly Ala Glu Leu
1               5                   10                  15

Gln Glu Arg Leu Cys Ala Ala His Lys Leu Cys His Pro Glu Glu Leu
            20                  25                  30

Met Leu Leu Arg His Ser Leu Gly Ile Pro Gln Ala Pro Leu Ser Ser
        35                  40                  45

Cys Ser Ser Gln Ser Leu Gln Leu Arg Gly Cys Leu Asn Gln Leu His
    50                  55                  60

Gly Gly Leu Phe Leu Tyr Gln Gly Leu Leu Gln Ala Leu Ala Gly Ile
65                  70                  75                  80

Ser Pro Glu Leu Ala Pro Thr Le
                85

<210> SEQ ID NO 42
<211> LENGTH: 88
<212> TYPE: PRT
<213> ORGANISM: Canis familiaris

<400> SEQUENCE: 42

```
Lys Cys Leu Glu Gln Met Arg Lys Val Gln Ala Asp Gly Thr Ala Leu
1               5                   10                  15

Gln Glu Thr Leu Cys Ala Thr His Gln Leu Cys His Pro Glu Glu Leu
            20                  25                  30

Val Leu Leu Gly His Ala Leu Gly Ile Pro Gln Pro Pro Leu Ser Ser
            35                  40                  45

Cys Ser Ser Gln Ala Leu Gln Leu Met Gly Cys Leu Arg Gln Leu His
    50                  55                  60

Ser Gly Leu Phe Leu Tyr Gln Gly Leu Leu Gln Ala Leu Ala Gly Ile
65                  70                  75                  80

Ser Pro Glu Leu Ala Pro Thr Leu
                85
```

<210> SEQ ID NO 43
<211> LENGTH: 88
<212> TYPE: PRT
<213> ORGANISM: Homo sapiens

<400> SEQUENCE: 43

```
Lys Cys Leu Glu Gln Val Arg Lys Ile Gln Gly Asp Gly Ala Ala Leu
1               5                   10                  15

Gln Glu Lys Leu Cys Ala Thr Tyr Lys Leu Cys His Pro Glu Glu Leu
            20                  25                  30

Val Leu Leu Gly His Ser Leu Gly Ile Pro Trp Ala Pro Leu Ser Ser
            35                  40                  45

Cys Pro Ser Gln Ala Leu Gln Leu Ala Gly Cys Leu Ser Gln Leu His
    50                  55                  60

Ser Gly Leu Phe Leu Tyr Gln Gly Leu Leu Gln Ala Leu Glu Gly Ile
65                  70                  75                  80

Ser Pro Glu Leu Gly Pro Thr Leu
                85
```

<210> SEQ ID NO 44
<211> LENGTH: 88
<212> TYPE: PRT
<213> ORGANISM: Mus musculus

<400> SEQUENCE: 44

```
Lys Ser Leu Glu Gln Val Arg Lys Ile Gln Ala Ser Gly Ser Val Leu
1               5                   10                  15

Leu Glu Gln Leu Cys Ala Thr Tyr Lys Leu Cys His Pro Glu Glu Leu
            20                  25                  30

Val Leu Leu Gly His Ser Leu Gly Ile Pro Lys Ala Ser Leu Ser Gly
            35                  40                  45

Cys Ser Ser Gln Ala Leu Gln Gln Thr Gln Cys Leu Ser Gln Leu His
    50                  55                  60

Ser Gly Leu Cys Leu Tyr Gln Gly Leu Leu Gln Ala Leu Ser Gly Ile
65                  70                  75                  80

Ser Pro Ala Leu Ala Pro Thr Leu
                85
```

<210> SEQ ID NO 45
<211> LENGTH: 88
<212> TYPE: PRT
<213> ORGANISM: Gallus gallus

<400> SEQUENCE: 45

-continued

```
Lys Asn Leu Glu Phe Thr Arg Lys Ile Arg Gly Asp Val Ala Ala Leu
 1               5                  10                 15

Gln Arg Ala Val Cys Asp Thr Phe Gln Leu Cys Thr Glu Glu Glu Leu
            20                  25                 30

Gln Leu Val Gln Pro Asp Pro His Leu Val Gln Ala Pro Leu Asp Gln
            35                  40                 45

Cys His Lys Arg Gly Phe Gln Ala Glu Val Cys Phe Thr Gln Ile Arg
        50                  55                 60

Ala Gly Leu His Ala Tyr His Asp Ser Leu Gly Ala Val Leu Arg Leu
65                  70                  75                 80

Leu Pro Asn His Thr Thr Leu Val
                85

<210> SEQ ID NO 46
<211> LENGTH: 89
<212> TYPE: PRT
<213> ORGANISM: Artificial Sequence
<220> FEATURE:
<223> OTHER INFORMATION: Consensus sequence

<400> SEQUENCE: 46

Lys Cys Leu Glu Met Ile Arg Tyr Ile Leu Gly Asp Ile Ser Ala Leu
 1               5                  10                 15

Arg Lys Glu Leu Cys Asp Thr Tyr Gln Leu Cys His Asn Glu Glu Glu
            20                  25                 30

Val Leu Ala Glu Asn Asn Leu Asn Leu Pro Lys Met Ala Glu Lys Asp
            35                  40                 45

Gly Cys Phe Gln Ser Gly Phe Asn Gln Glu Thr Cys Leu Thr Gln Ile
        50                  55                 60

Thr Thr Gly Leu Met Glu Tyr Gln Ile Tyr Leu Glu Tyr Leu Gln Asn
65                  70                  75                 80

Asn Tyr Pro Gly Asn Lys Glu Asn Val
                85
```

NUCLEIC ACIDS ENCODING CYTOKINE-LIKE PROTEINS THAT PROMOTE CELL PROLIFERATION

CROSS-REFERENCE TO RELATED APPLICATIONS

This application is a divisional application of and claims priority under 35 USC §120 of U.S. application Ser. No. 09/687,637, filed Oct. 13, 2000 now U.S. Pat. No. 6,610, 285, which is a continuation-in-part of International Patent Application No. PCT/JP99/01997, filed Apr. 14, 1999, and claims priority from Japanese Patent Application No. 10/121805, filed Apr. 14, 1998, the disclosures of which are incorporated herein by reference in their entirety.

FIELD OF THE INVENTION

This invention relates to a novel cytokine-like protein and the encoding genie.

Background of the Invention

Cytokines are multi-functional cell growth/differentiation inducing factors controlling immune and hematopoietic reactions. The series of factors composing cytokines, are mainly produced by activated T cells, macrophages, or stromal cells and connect the cells of the lymphoid system and the hematopoietic system in a network, regulating the proliferation, differentiation, and functions of these cells. So far, a number of factors have been isolated as cytokines and apart from the factors themselves, antibodies and receptor molecules of those factors, or antibodies against those receptors, have been developed as therapeutic drugs and are in actual use.

For example, G-CSF, which has a neutrophil-proliferating function, is already in use as a drug for many diseases and leukopenia resulting from the treatment of these diseases (K. Welte et al., the first 10 years Blood Sep. 15 1996; 88:1907–1929 and also refer GENDAIKAGAKU ZOU-KAN no. 18, Cytokine, edited by TOSHIAKI OHSAWA, 1990, published by TOKYO KAGAKU DOUJIN). Furthermore, an antibody against the receptor of IL-6, which acts in immune functions and inflammation, is being developed as a potential therapeutic drug against rheumatism and leukemia.

Summary of the Invention

The present invention provides a novel cytokine-like protein and the encoding DNA. It also provides a vector into which the DNA has been inserted, a transformant carrying the DNA, and also a method for producing a recombinant protein using the transformant. Furthermore, screening methods for a compound, which binds to the protein and regulates the activity, and the uses of the protein and the compounds regulating its function as pharmaceutical drugs, are also provided by the present invention.

Most cytokines known so far, have a conserved characteristic such as a WS Motif (Idzerda, RL et al., J Exp Med 1990 Mar 1; 171 (3) 861–873), and form a super-family of cytokine receptors. Although the cytokine itself, which is the ligand, does not have a conserved characteristic or homology compared to the receptor, some groups have an extremely weak homology, hinting of a close stereoscopic structure. EPO/TPO family and IL-6/G-CSF/MGF family can be taken as examples. The present inventors, thinking that unknown, yet unidentified genes may exist in these families, attempted to isolate an unknown cytokine belonging to these families.

Specifically, it was found that the EST (AA418955) sequence, which does not show any homology to other proteins in the Database, has a weak homology to G-SCF and constructed primers based on that sequence, and did PCR cloning from a human fetal spleen library. As a result, the present inventors succeeded in isolating a full-length cDNA corresponding to the EST (this clone was named SGRF). Also, the isolated SGRF cDNA was sequenced and the structure analyzed to find that the isolated cDNA has the typical characteristics of a factor belonging to the IL-6/G-CSF/MGF family. Furthermore, the inventors analyzed the activity of the SGRF protein to find that the culture supernatant of SGRF-transfected CHO cells has a proliferation supporting activity towards specific bone marrow cells in the presence of mouse kit ligand. The isolated SGRF protein itself may be applicable for the prevention and treatment of diseases of the lymphoid and hematopoietic systems and for diseases related to defective cell growth. Also it is possible to use this protein for the screening of other factors related to the lymphoid and hematopoietic systems and as a drug candidate compound for diseases of those systems.

Namely, this invention relates to a novel cytokine-like protein SGRF and the encoding gene, their production as well as the use of the protein in the screening of drugs and drug candidate compounds. More specifically, 1. a protein comprising the amino acid sequence of SEQ ID NO:1, or said sequence in which one or more amino acids are replaced, deleted, added, and/or inserted, 2. a protein encoded by a DNA hybridizing with the DNA comprising the nucleotide sequence of SEQ ID NO:2, which is functionally equivalent to the protein having the amino acid sequence of SEQ ID NO:1, 3. a DNA encoding the protein of (1) or (2), 4. the DNA of (3), which contains the coding region of the nucleotide sequence of SEQ ID NO:2, 5. a vector in which the DNA of (3) or (4) is inserted, 6. a transformant carrying, in an expressible manner, the DNA of (3) or (4), 7. a method for producing the protein of (1) or (2), which comprises the culturing of the transformant of (6), 8. a method for screening a compound which can bind to the protein of (1) or (2), the method comprising the steps of:

(a) exposing a test sample to the protein of (1) or (2) or its partial peptide;

(b) detecting the binding activity between the test compound and said protein or its partial peptide; and (c) selecting a compound having a binding activity to said protein, 9. a compound which can bind to the protein of (1) or (2), 10. the compound of (9) which is obtainable by the method of (8), 11. a method for screening a compound which can promote or inhibit activity of the protein of (1) or (2), the method comprising the steps of:

(a) exposing the protein of (1) or (2) and the kit ligand to mammalian bone marrow cells under the absence of a test compound;

(b) detecting the proliferation of said bone marrow cells; and (c) selecting a compound which promotes or inhibits the proliferation of bone marrow cells in comparison with the assay under the presence of the test sample, 12. the method of (11), wherein the bone marrow cells are Lin negative, Sca-1 positive, c-kit positive, and CD34 positive, 13. a compound which promotes or inhibits the activity of the protein of (1) or (2), 14. the compound of (13) which is obtainable by the method of (11) or (12), 15. a pharmaceutical composition comprising the protein of (1) or (2) as an active component, 16. a promoter or inhibitor of the protein of (1) or (2) wherein the active component is the compound of (13) or (14), 17. an antibody which can bind to the protein of (1) or (2), and 18. a DNA comprising at least 15 nucleotides, which can specifically hybridize with the DNA comprising the nucleotide sequence of SEQ ID NO:2.

The present invention relates to a novel cytokine-like protein. The nucleotide sequence of the cDNA encoding the protein named "SGRF", which is included in the protein of the present invention is shown in SEQ ID NO:2; the amino-acid sequence of said protein in SEQ ID NO:1.

So far, in mammals, IL-6 and G-CSF have been reported as factors thought to belong to the IL-6/G-CSF/MGF family. The "SGRF" cDNA isolated by the present inventors, had in its 3' non-coding region, four mRNA destabilizing sequences (Lagnando CA, Brown CY, Goodall GJ (1994) Mol. Cell. Biol. 14, 7984–7995) called ARE (AT Rich element), often seen in cytokine mRNAs. The consensus sequence preserved in the IL-6/G-CSF/MGF family was also roughly maintained (FIG. 3). From these facts, "SGRF" can be assumed to be a novel factor belonging to the IL-6/G-CSF/MGF family.

The "SGRF" expression in human normal tissue as detected by northern-blot analysis is extremely localized, and was seen in the testis, lymph nodes, and thymus, being not present in a detectable level in other tissues (FIG. 4). Even in tissues where expression was detected, the expression level was assumed to be very low. An EST (U38443), a partial fraction of "SGRF", which is normally hardly expressed, is reportedly induced following activation in a T cell-line (Jurkat) (Yatindra Prashar, Sherman M. Weissman (1996) Proc. Natl. Acad. Sci. USA 93:659–663). From this fact and from the results of northern-blot analysis, it can be assumed that in vivo, "SGRF" is mainly expressed in activated T cells.

Furthermore, the culture supernatant of "SGRF" transfected CHO cells showed an activity, which supported the proliferation of bone marrow cells (FIG. 12), in the presence of the kit ligand.

The characteristics of "SGRF" such as those above, suggest that it is a kind of a typical interleukin. "SGRF", as are most cytokines isolated so far, is thought to be involved in the lymphoid and hematopoietic systems. Therefore, it can be applied as a therapeutic or preventive drug in diseases of the lymphoid and hematopoietic systems, and also in diseases associated with defects in cell proliferation.

The protein of the present invention can be prepared by methods commonly known to one skilled in the art, as a recombinant protein made using genetic engineering techniques, and also as a natural protein. For example, a recombinant protein can be prepared by, inserting DNA encoding the protein of the present invention (for example, DNA comprising the nucleotide sequence in SEQ ID NO:1) into a suitable expression vector, introducing this into a host cell, and purifying the protein from the resulting transformant or the culture supernatant. The natural protein can be prepared by immobilizing in a column, antibodies taken from immunizing a small animal with the recombinant protein, and performing affinity chromatography for extracts of tissues or cells (for example, testis, lymph nodes, thymus, etc.) expressing the protein of the present invention.

Also, this invention features a protein, which is functionally equivalent to the "SGRF" protein (SEQ ID NO:1). The method of inserting a mutation into the amino acids of a protein is a well-known method for isolating such proteins. In other words, for a person skilled in the art, the preparation of a protein functionally equivalent to the "SGRF" protein, is something which can be generally done using various methods such as the PCR-mediated, site-specific-mutation-induction system (GIBCO-BRL, Gaithersburg, Md.), oligo-nucleotide-mediated, site-specific-mutation-induction method (Kramer, W. and Fritz, HJ (1987) Methods in Enzymol., 154:350–367) suitably replacing amino acids in the "SGRF" protein shown in SEQ ID NO:1, which do not influence the function. Mutations of amino acids can occur spontaneously as well. Therefore, the protein of the invention includes those proteins that are functionally equivalent to the "SGRF" protein, having an amino acid sequence in which one or more amino acids in the amino acid sequence of the "SGRF" protein (SEQ ID NO:1) have been replaced, deleted, added, and/or inserted. The term "functionally equivalent" as used herein, refers to a protein having a cytokine activity equivalent to that of the "SGRF" protein. The cytokine activity of the "SGRF" protein includes, for example, a proliferation-supporting activity (Example 11) towards cells which are Lin negative, Sca-1 positive and c-kit positive.

The number of amino acids that are mutated is not particularly restricted, as long as a cytokine activity equivalent to that of the "SGRF" protein is maintained. Normally, it is within 50 amino acids, preferably within 30 amino acids, more preferably within 10 amino acids and even more preferably within 5 amino acids. The site of mutation may be any site, as long as a cytokine activity equivalent to that of the "SGRF" protein is maintained.

A "conservative amino acid substitution" is one in which an amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In the present invention, the protein having numerous depletions in the amino acid sequence of the "SGRF" protein (SEQ ID NO:1) includes a partial peptide. The partial peptide includes, for example, a protein of which the signal peptide has been excluded from the "SGRF" protein of SEQ ID NO:1.

Also, a fusion protein can be given as a protein comprising the amino acid sequence of the "SGRF" protein and several amino acids added thereto. Fusion proteins are, for example, fusions of the above described proteins and other peptides or proteins, and are included in the present invention. Fusion proteins can be made by techniques commonly known to a person skilled in the art, such as linking the DNA encoding the protein of the invention and with DNA encoding other peptides or proteins, so as the frames match, inserting this into an expression vector and expressing it in a host. There is no restriction as to the peptides or proteins fused to the protein of the present invention.

Commonly known peptides, for example, FLAG (Hopp, T.P. et al., Biotechnology (1988) 6:1204–1210), 6×His constituting six His (histidine) residues, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment can be used as peptides that are fused to the protein of the present invention. Examples of proteins that are fused to protein of the invention are, GST (glutathione-S-transferase), HA (Influenza agglutinin), Immunoglobulin constant region, β-galactosidase and MBP (maltose-binding protein). Fusion proteins can be prepared by fusing commercially available DNA encoding these peptides or proteins with the DNA encoding the protein of the present invention and expressing the fused DNA prepared.

The hybridization technique (Sambrook, J. et al., Molecular Cloning 2nd ed. 9.47–9.58, Cold Spring Harbor Lab. press, 1989) is well known to one skilled in the art as an alternative method for isolating a protein functionally equivalent to the "SGRF" protein (SEQ ID NO:1). In other words, for a person skilled in the art, it is a general procedure to prepare a protein functionally equivalent to the "SGRF" protein, by isolating DNA having a high homology with the whole or part of the DNA encoding the "SGRF" protein used as a base for the preparation of the protein. Therefore, the protein of the present invention also includes proteins, which are functionally equivalent to the "SGRF" protein and are encoded by DNA hybridizing with DNA encoding the "SGRF" protein. The term "functionally equivalent" as used herein, means as mentioned above, proteins that show a cytokine activity equivalent to that of the "SGRF" protein. Apart from humans, for example, mice, rats, cows, monkeys and pigs can be used as animals from which functionally equivalent proteins can be isolated. One skilled in the art can suitably select the stringency of hybridization for isolating DNA encoding a functionally equivalent protein, but normally, it is equilibrium hybridization at about 42° C., 2×SSC, 0.1% SDS (low stringency); about 50° C., 2×SSC, 0.1% SDS (medium stringency); or about 65° C., 2×SSC, 0.1/% SDS (high stringency). If washings are required to reach equilibrium, then the washings are performed using the same buffer as the original hybridization solution, a listed above. In general, the higher the temperature, the higher is the homology of the DNA obtainable. "High homology" refers to, in comparison with the amino acid sequences of the "SGRF" protein, normally a homology of 40% or higher, preferably 60% or higher, more preferably 80% or higher, even more preferably 95% or higher. The homology of a protein can be determined by following the algorithm in Wilbur, W. J. and Lipman, D. J. Proc. Natl. Acad. Sci. USA (1983) 80:726–730.

The "percent identity" of two amino acid sequences or of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12. BLAST protein searches are performed with the XBLAST program, score=50, wordlength=3. Where gaps exist between two sequences, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. See http://www.ncbi.nlm.nih.gov.

This invention also relates to a DNA encoding the above protein. There is no particular restriction as to the DNA of the present invention as long as it encodes the protein of the present invention and includes cDNA, genomic DNA and chemically synthesized DNA. cDNA can be prepared by, making a primer using the nucleotide sequence of the "SGRF" cDNA, disclosed in SEQ ID NO:2, and performing RT-PCR using the mRNA prepared from cells expressing the "SGRF" protein as the template. In the case of genomic DNA, preparation can be done by the plaque hybridization method using a genomic DNA inserted λ phage library and the cDNA probe obtained. The nucleotide sequence of the DNA acquired can be decided by ordinary methods in the art using the commercially available "dye terminator sequencing kit" (Applied Biosystems). The DNA of the present invention, as stated later, can be utilized for the production of a recombinant protein and gene therapy.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally Occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones: e.g., as these occur in a DNA library such as a cDNA or genomic DNA library.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

The present invention also features a vector into which the DNA of the present invention has been inserted. There is no restriction as to the vector to which DNA is inserted, and various vectors such as those for expressing the protein of the present invention in vivo and those for preparing the recombinant protein can be used according to the objective. To express the protein of the present invention in vivo (especially for gene therapy), various viral vectors and non-viral vectors can be used. Examples of viral vectors are, adenovirus vectors (pAdexLcw and such) and retrovirus vectors (pZIPneo and such). Expression vectors are especially useful when using vectors for the objective of producing the protein of the invention. For example, when using *Escherichia coli* the "pQE vector" (Qiagen, Hilden, Germany), when using yeast "SP-Q01" (Stratagene, La Jolla, Calif.), when using insect cells "Bac-to-Bac baculovirus expression system" (GIBCO-BRL, Gaithersburg, Md.)

are highly appropriate, but there is no restriction. Also, when using mammalian cells such as CHO cells, COS cells, NIH3T3 cells, for example, the "LacSwitch II expression system (Stratagene, La Jolla, Calif.) is highly suitable, but there is no restriction. Insertion of the DNA of the present invention into a vector can be done using ordinary methods in the art.

The present invention also refers to a transformant, carrying, in an expressible manner, the DNA of the present invention. The transformant of the present invention includes, those carrying the above-mentioned vector into which DNA of the present invention has been inserted, and those host genomes into which the DNA of the present invention has been integrated. As long as the DNA of the present invention is maintained in an expressible manner, no distinction is made as to the form of existence of the transformants. There is no particular restriction as to the cells into which the vector is inserted. When using the cells to express the protein of the present invention for the purpose of gene therapy by the ex vivo method, various cells (for example, various cells of the immune system) can be used as target cells according to the type of disease. Also, when the purpose is to produce the protein of the present invention, for example, E. coli, yeast, animal cells and insect cells can be used in combination with the vectors that are utilized. Introduction of a vector into a cell can be done using commonly known methods such as electroporation and calcium phosphate method.

The separation and purification of the recombinant protein from the transformant made to produce the protein can be done using ordinary methods. The recombinant protein can be purified and prepared by, for example, ion exchange chromatography, reverse phase chromatography, gel filtration, or affinity chromatography where an antibody against the protein of the present invention has been immobilized in the column, or by combining two or more of these columns. Also when expressing the protein of the present invention inside host cells (for example, animal cells and E. coli) as a fusion protein with glutathione-S-transferase protein or as a recombinant protein supplemented with multiple histidines, the expressed recombinant protein can be purified using a glutathione column or nickel column. After purifying the fusion protein, it is also possible to exclude regions other than the objective protein by cutting with thrombin or factor-Xa as required.

The present invention also features an antibody binding to the protein of the invention. There is no particular restriction as to the form of the antibody of the present invention and include, apart from polyclonal antibodies, monoclonal antibodies as well. The antiserum obtained by immunizing animals such as rabbits with the protein of the present invention, polyclonal and monoclonal antibodies of all classes, humanized antibodies made by genetic engineering, human antibodies, are also included., The antibodies of the present invention can be prepared by the following methods. Polyclonal antibodies can be made by, obtaining the serum of small animals such as rabbits immunized with the protein of the present invention, attaining a fraction recognizing only the protein of the present invention by an affinity column coupled with the protein of the present invention, and purifying immunoglobulin G or M from this fraction by a protein G or protein A column. Monoclonal antibodies can be made by immunizing small animals such as mice with the protein of the present invention, excising the spleen from the animal, homogenizing the organ into cells, fusing the cells with mouse bone marrow cells using a reagent such as polyethylene glycol, selecting clones that produce antibodies against the protein of the invention from the fused cells (hybridomas), transplanting the obtained hybridomas into the abdominal cavity of a mouse, and extracting ascites. The obtained monoclonal antibodies can be purified by, for example, ammonium sulfate precipitation, protein A or protein G column, DEAE ion exchange chromatography, or an affinity column to which the protein of the present invention is coupled. The antibody of the invention can be used for purifying and detecting the protein of the invention. It can also be used as a pharmaceutical drug to control the function of the present protein. When using the antibody as a drug for humans, in the point of immunogenicity, the human antibodies or the humanized antibodies are effective. The human antibodies or humanized antibodies can be prepared by methods commonly known to one skilled in the art. For example, human antibodies can be prepared by, immunizing a mouse whose immune system has been changed to that of humans, using the protein of the invention. Also, humanized antibodies can be prepared by, for example, cloning the antibody gene from monoclonal antibody producing cells and using the CDR graft method which transplants the antigen-recognition site of the gene into an already known human antibody.

The present invention also relates to a method for screening a chemical compound that binds to the protein of the invention. The screening method of the invention includes the steps of, (a) exposing a test sample to the protein of the invention, (b) detecting the binding activity between the test sample and the protein of the invention, and (c) selecting a compound having an activity to bind to the protein of the invention. Any test sample call be used without particular restrictions. Examples are, synthetic low molecular weight compound libraries, purified proteins, expression products of gene libraries, synthetic peptide libraries, cell extracts, and culture supernatants. Selection of a compound that has an activity to bind to the protein of the invention can be done using methods commonly known to one skilled in the art.

The screening of a protein which binds to the protein of the invention can be done by, for example, creating a cDNA library from tissues or cells (for example, testis, lymph nodes and thymus) predicted to express a protein binding to the protein of the invention using a phage vector (λgt11 and Zap11), expressing this cDNA library on LB-agarose, fixing the expressed proteins on the filter, biotin-labeling the protein or the invention or purifying it as a fusion protein with GST protein, reacting this with the above-described filter, and detecting plaques expressing the binding proteins using streptavidin or anti-GST antibody (West Western Blotting method) (Skolnik E Y, Margolis B, Mohammadi M, Lowenstein E, Fischer R, Drepps A, Ullrich A, and Schlessinger J (1991) Cloning of PI3 kinase-associated p85 utilizing a novel method for expression/cloning of target proteins for receptor tyrosine kinases. Cell 65:83–90).

The screening of a protein binding to the protein of the invention or the gene of the protein, can also be done by following "the two hybrid system" ("MATCHMAKER Two-hybrid System", "Mammalian MATCHMAKER Two-hybrid Assay Kit", "MATCHMAKER One-Hybrid System" (Clontech), "HybriZAP Two-Hybrid Vector System" (Stratagene), Reference, "Dalton, S. and Treisman, R. (1992) Characterization of SAP-1, a protein recruited by serum response factor to the c-fos serum response element. Cell 68:597–612"). Namely, the protein of the invention is fused to the SRF binding region or GAL4 binding region and expressed in yeast cells. A cDNA library, is prepared from cells predicted to express a protein binding to the protein of the invention so as to express the ligand fused to the VP16 or GaL4 transcriptional activation region. The cDNA library is then introduced into the above yeast cells and the cDNA derived from the library is isolated from the positive clones detected (when a protein binding to the protein of the invention is expressed in yeast cells, the binding of the two activates a reporter gene making positive clones detectable). The isolated cDNA is expressed by introducing it into *E. coli* to obtain a protein encoded by the cDNA. Furthermore, a protein binding to the protein of the invention can be screened by, applying the culture supernatants or cell extracts of cells predicted to express a protein binding to the protein of the invention onto an affinity column in which the protein of the invention is immobilized and purifying the protein that binds specifically to the column.

Also, the method of screening molecules which bind when the immobilized protein of the invention is exposed to synthetic chemical compounds, or natural substance banks, or a random phase peptide display library, or the method of screening using high-thoughput based on combinatorial chemistry techniques (Wrighton NC; Farrel FX; Chang R; Kashyap AK; Barbone FP; Mulcahy LS; Johnson DL; Barret RW; Jolliffe LK; Dower WJ. Small peptides as potent mimetics of the protein hormone erythropoietin, Science (UNITED STATES) Jul. 26 1996, 273 p458–68, Verdine GL., The combinatorial chemistry of nature. Nature (ENGLAND) Nov. 7 1996, 384 p11–13, Hogan JC Jr., Directed combinatorial chemistry Nature (ENGLAND) Nov. 7 1996, 384 p17–9) to isolate low molecular weight compounds, proteins (or the genes) and peptides are methods well known to one skilled in the art.

The present invention also relates to a method for screening a compound able to promote or inhibit the activity of the protein of the invention. It was found that the protein of the invention has a proliferation-supporting activity for bone marrow cells in the presence of the kit ligand. Therefore, using this activity as an indicator, screening of a compound able to promote or inhibit activity of the protein of the invention can be performed. Namely, this screening can be done using the method comprising the steps of: (a) exposing the protein of the invention and the kit ligand to mammalian bone marrow cells under the presence of a test compound; (b) detecting the proliferation of the bone marrow cells; and (c) selecting a compound which promotes or inhibits the proliferation of bone marrow cells when compared with the assay in the absence of a test sample (control).

There are no particular restrictions as to the test sample used. Examples are, libraries of synthetic low molecular compounds, purified proteins, expression products of gene libraries, synthetic peptide libraries, cell extracts and culture supernatants. The compound isolated by the above-described screening of a protein binding to the protein of the invention may also be used as a test compound.

The protein of the present invention and the kit ligand may be recombinant or natural proteins. Also, as long as the activity is maintained, may be a partial peptide. The kit ligand may also be a commercially available one.

Lin negative, Sca-1 positive and c-kit positive bone marrow cells are preferred for the screening. Bone marrow cells that are additionally CD34 positive are preferred more.

The culture conditions and detection of proliferation of bone marrow cells can be done, for example, in conformance with Example 11.

As a result of the detection, compared with the proliferation of bone marrow cells in the absence of the test compound (control), if the proliferation of bone marrow cells is suppressed with the addition of a test compound, then the test compound is judged to be a compound (or includes the compound), which inhibits the activity of the protein of the invention. On the other hand, if the proliferation is promoted by the addition of the test compound (or includes the compound), it is judged to be a compound that promotes the activity of the protein of the invention.

The protein of the present invention can be used as a reagent in research to control the proliferation of cells of the lymphoid and hematopoietic systems. The compound isolated by the above-mentioned screening, can be used as an inhibitor or promoter of the protein in the invention. Moreover, the protein of the invention or these compounds can also be utilized as drugs for the prevention and therapy of diseases associated with defects in cell proliferation and lymphoid and hematopoietic systems.

When using the protein of the invention or a compound that controls the activity of the protein as drugs, they can be formulated into a dosage formulated using commonly known pharmaceutical preparation methods. For example, according to the need, the drugs can be taken orally (as sugar-coated tablets, capsules, elixirs and microcapsules) or non-orally (such as, percutaneously, intranasally, bronchially, intramuscularly and intravenously) in the form of injections of sterile solutions or suspensions with water or any other pharmaceutically acceptable liquid. For example, the protein of the invention or compounds controlling the activity of the protein can be mixed with physiologically acceptable carriers, flavoring agents, excipients, vehicles, preservatives, stabilizers and binders, in a unit dose form required for generally accepted drug implementation. The amount of active ingredients in these preparations makes a suitable dosage within the indicated range acquirable.

Examples for additives which can be mixed to tablets and capsules are, binders such as gelatin, corn starch, tragacanth gum and arabic gum; excipients such as crystalline cellulose; swelling agents such as cornstarch, gelatin and alginic acid; lubricators such as magnesium stearate; sweeteners such as sucrose, lactose or saccharin; flavoring agents such as peppermint, Gaultheria adeuothrix oil and cherry. When the unit dosage form is a capsule, a liquid carrier, such as oil, can also be included in the above ingredients. Sterile composites for injections can be formulated following normal drug implementations using vehicles such as distilled water used for injections.

Physiological saline, glucose, and other isotonic liquids including adjuvants, such as D-sorbitol, D-mannose, D-mannitol, and sodium chloride, can be used as aqueous solutions for injections. These can be used in conjunction with suitable solubilizers, such as alcohol, specifically ethanol, polyalcohols such as propylene glycol and poly ethylene glycol, non-ionic surfactants, such as Polysorbate 80 (TM) and HCO-50.

Sesame oil or soy-bean oil can be used as a oleaginous liquid and may be used in conjunction with benzyl benzoate or benzyl alcohol as a solubilizer; may be formulated with a buffer such as phosphate and sodium acetate; a pain-killer such as procaine hydrochloride; a stabilizer such as benzyl alcohol, phenol, and an anti-oxidant. The prepared injection is filled into a suitable ampule.

One skilled in the art can suitably select the dosage and method of administration according to the body-weight, age, and symptoms of a patient.

For example, although there are some differences according to the patient, target organ, symptoms and method of administration, the dose is about 1 µg to about 100 mg per day for a normal adult (weight 60 kg) when the protein is given as an injection.

For a compound controlling the activity of the protein of the invention, although it can vary according to the symptoms, the dosage is about 0.1 to about 100 mg per day, preferably about 0.1 to about 50 mg per day and more preferably about 0.1 to about 20 mg per day, when administered orally.

When administering non-orally in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kg of body-weight.

This invention also features a DNA containing at least 15 nucleotides, which can specifically hybridize with DNA encoding the "SGRF" protein. The term "specifically hybridize" as used herein, indicates that cross-hybridization does not occur significantly with DNA encoding other proteins, in the above-mentioned hybridizing conditions, preferably under stringent hybridizing conditions.

Such DNA can be utilized to detect DNA encoding the "SGRF" protein, as an isolation probe, and also as a primer for amplification. Specifically, the primers in SEQ ID NOs:3 to 20 can be given as examples. Such DNA can also be used as an oligo nucleotide or a ribozyme.

An antisense oligonucleotide is preferably an antisense oligonucleotide against at least 15 continuous nucleotides in the nucleotide sequence of SEQ ID NO:2. The above-mentioned antisense oligonucleotide, which contains an initiation codon in the above-mentioned at least 15 continuous nucleotides, is even more preferred.

Derivatives or modified products of antisense oligonucleotides can be used as antisense oligonucleotides. Examples are, lower class alkyl phosphate modifications such as methyl-phosphonate-type or ethyl-phosphonate-type and phosphothioate or phosphoramidate.

The term "antisense oligonucleotides" as used herein means, not only those in which the nucleotides corresponding to those constituting a specified region of a DNA or mRNA are complementary, but also those having a mismatch of one or more nucleotides, as long as DNA or mRNA and an oligonucleotide can specifically hybridize with the nucleotide sequence of SEQ ID NO:2.

Such DNAs are indicated as those having, in the "at least 15 continuous nucleotide sequence region", a homology of at least 70% or higher, preferably at 80% or higher, more preferably 90% or higher, even more preferably 95% or higher to the nucleotide sequence of SEQ ID NO:2. The algorithm stated herein can be used to determine homology.

The antisense oligonucleotide derivative of the present invention, acts upon cells producing the protein of the invention by binding to the DNA or mRNA encoding the protein and inhibits its transcription or translation, promotes the degradation of the mRNA, inhibiting the expression of the protein of the invention resulting in the inhibition of the protein's function.

The antisense oligonucleotide derivative of the present invention can be made into an external preparation such as a liniment and a poultice by mixing with a suitable base material, which is inactive against the derivatives.

Also, as needed, the derivatives can be formulated into tablets, powders, granules, capsules, liposome capsules, injections, solutions, nose-drops and freeze-drying agents by adding excipients, isotonic agents, dissolving auxiliaries, stabilizers, preservatives and pain-killers. These can be prepared using usual methods.

The antisense oligonucleotide derivative is given to the patient by, directly applying onto the ailing site or by injecting into a blood vessel so that it will reach the site of ailment. An antisense-mounting medium can also be used to increase durability and membrane-permeability. Examples are, liposome, poly-L lysine, lipid, cholesterol, lipofectin or derivatives of these.

The dosage of the antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

BRIEF DESCRIPTION OF THE DRAWINGS

FIG. 1 shows the "SGRF" cDNA nucleotide sequence together with the deduced amino acid sequence. The mRNA destabilizing sequence is underlined.

FIG. 2 shows the alignment of the consensus sequence of "SGRF" and proteins belonging to the IL-6/G-CSF/MGF family. The consensus sequence of this family is thought to be C-x(9)-C-x(6)-G-1-x(2)-[FY]- x(3)-L, is well preserved in "SGRF" as well, excluding the point that the number of the first x is 11 instead of 9. In the figure, Sooty Mangabey is an animal of the Cercocebus species and Rhesus Macaque is of the Rhesus Monkey species.

FIG. 6 shows the amino acid sequence of a protein presumed to be the genomic DNA nucleotide sequence of SGRF. Introns are shown in simple letters, exons in capitals. Sequences expected to be those of the TATA Box and poly A addition signal are underlined.

FIG. 11 shows the pLG-SGRFg map.

DETAILED DESCRIPTION OF THE INVENTION

The present invention will be explained in detail below with reference to examples, but it is not limited thereto.

EXAMPLE 1

Isolation of the "SGRF" Gene

When the GenBank EST database was searched by means of TBLAST using the human G-CSF protein sequence, the EST of Reg. No: AA418955 showed a weak homology to G-CSF. Based on this sequence, when an EST sequence considered to be reading the same gene was searched, four other registered ESTs (AA418747, U38443, AA729815, AA418955) were found. These sequences were aligned using DNASIS, the consensus sequence was extracted, and the following primers were designed:

"ILX-1"(GAGAAGAGGGAGATGAAGAGACTAC/SEQ.ID.NO:3);

"ILX-2"(CTGAGTCCTTGGGGGTCACAGCCAT/SEQ.ID.NO:4);

"ILX-3"(GTGGGACCTGCATATGTTGAAAATT/SEQ.ID.NO:5;

"ILX-4"(CCCCAAATTTCCCTTCCCATCTAATA/SEQ.ID.NO:6);

"ILX-5"(CCCTACTGGGCCTCAGCCAACTCCT/SEQ.ID.NO:7);

and

"ILX-6"(GGAGCAGAGAAGGCTCCCCTGTGAA/SEQ.ID.NO:8.

Using the human fetal spleen library (Marathon-Ready cDNA; Clontech), sequential PCR was performed in combinations of primers stated below, divided into 3 fragments, and amplified separately (5'side, central area, and 3'side). The primers used for the 5'side amplification were, "AP1" (Clontech) and "ILX-6" in the primary PCR, "AP2" (Clontech) and "ILX-2" in the nested PCR. As to the central area, "ILX-1" and "ILX-4" were used for the primary and nested PCRs. For the 3' side, "AP1" (Clontech) and "ILX-5" were used in the primary PCR, "AP2" (Clontech) and "ILX-3" in the nested PCR. Amplifications by both the primary and nested PCRs were done under conditions in which those recommended by the Manufacturer were partially changed (touchdown PCR: 1 min at 96° C., following 30 sec at 96° C., 5 cycles of "4 min at 72° C.", following 30 sec at 96° C., 5 cycles of the "4 min at 70° C.", following 20 sec at 96° C. and 26 cycles of "4 mil at 68° C.". However, TaKaRa Ex Taq (Takara Shuzo) and attached buffers were used instead of Advantage Klentaq Polyerase Mix). The obtained DNA were then electrophoresed on agarose gel, the corresponding bands were cut-off, after purifying by QIAEX II Gel Extraction Kit (QIAGEN), were cloned into the plasmid pT7Blue (R) T-vector (Novagen). The obtained plasmids were named pT7Blue-ILX1–4 (the vector which cloned the central area), pT7Blue-ILX5' (the vector which cloned the 5'end area), and pT7Blue-ILX3' (the vector which cloned the 3'end area), respectively. Each nucleotide sequence cloned was determined using ABI PRISM Dye Terminator Cycle Sequencing Ready Reaction Kit with Amplitaq DNA Polymerase FS and 377 A DNA Sequencer (Perkin-elmer).

Figure 2:
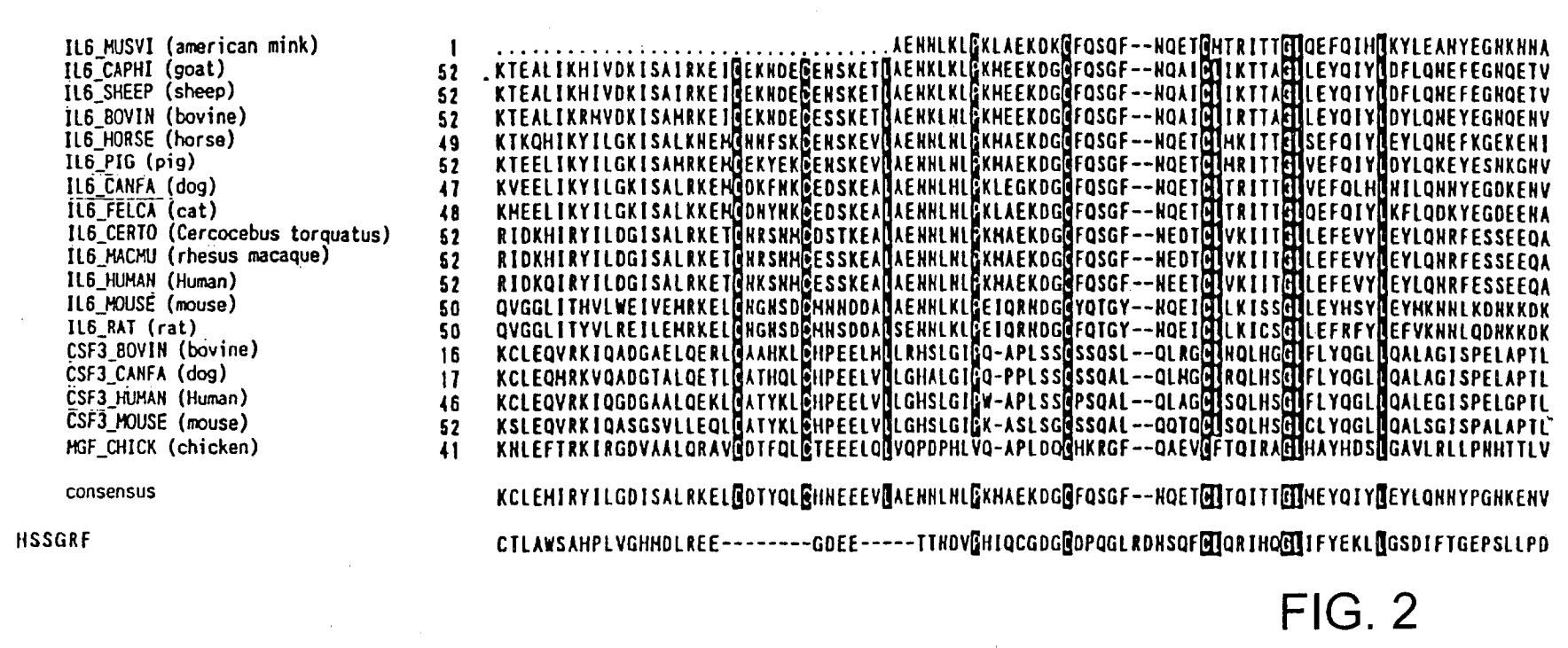
Figure 3:
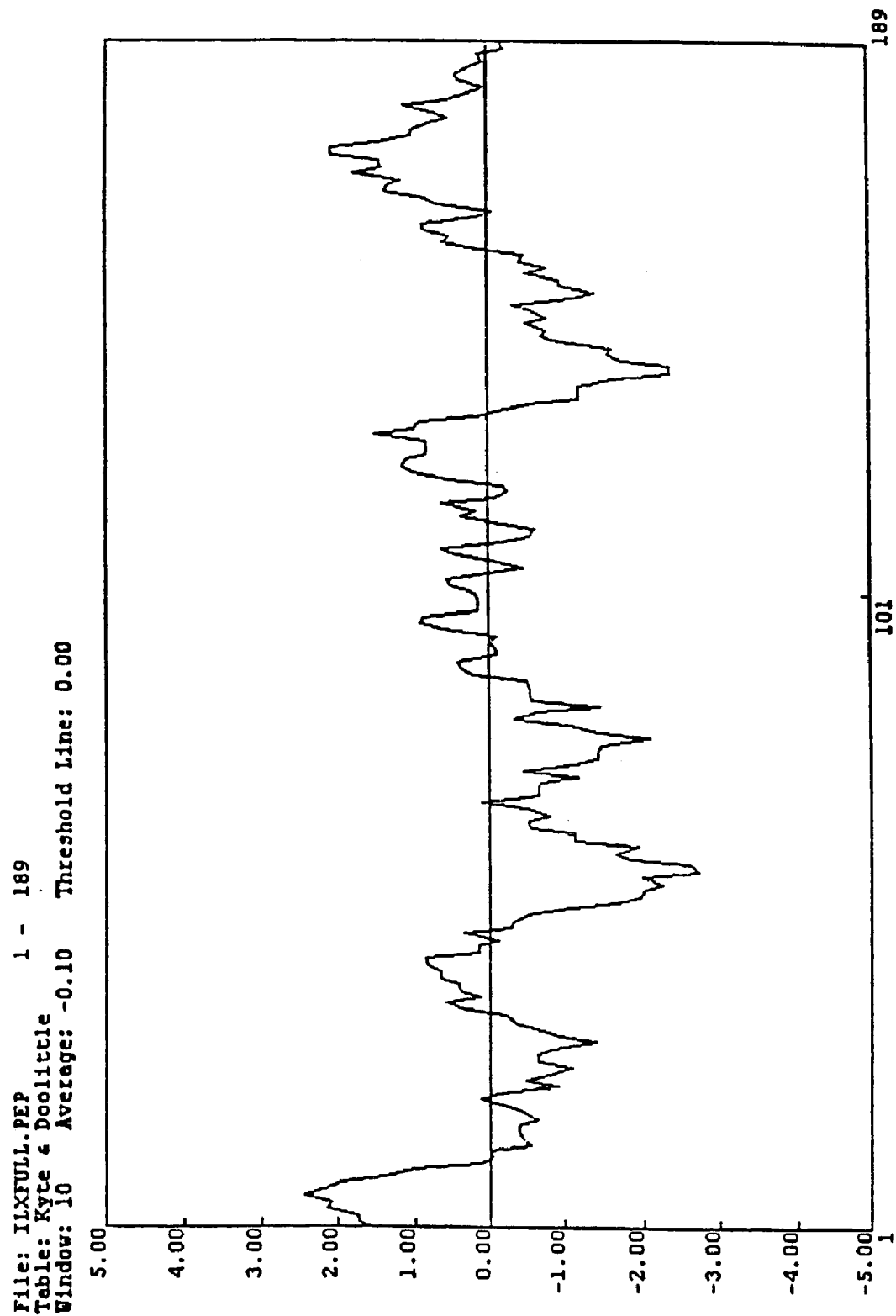
FIG. 3 shows the hydrophobicity of "SGRF".
Figure 4:
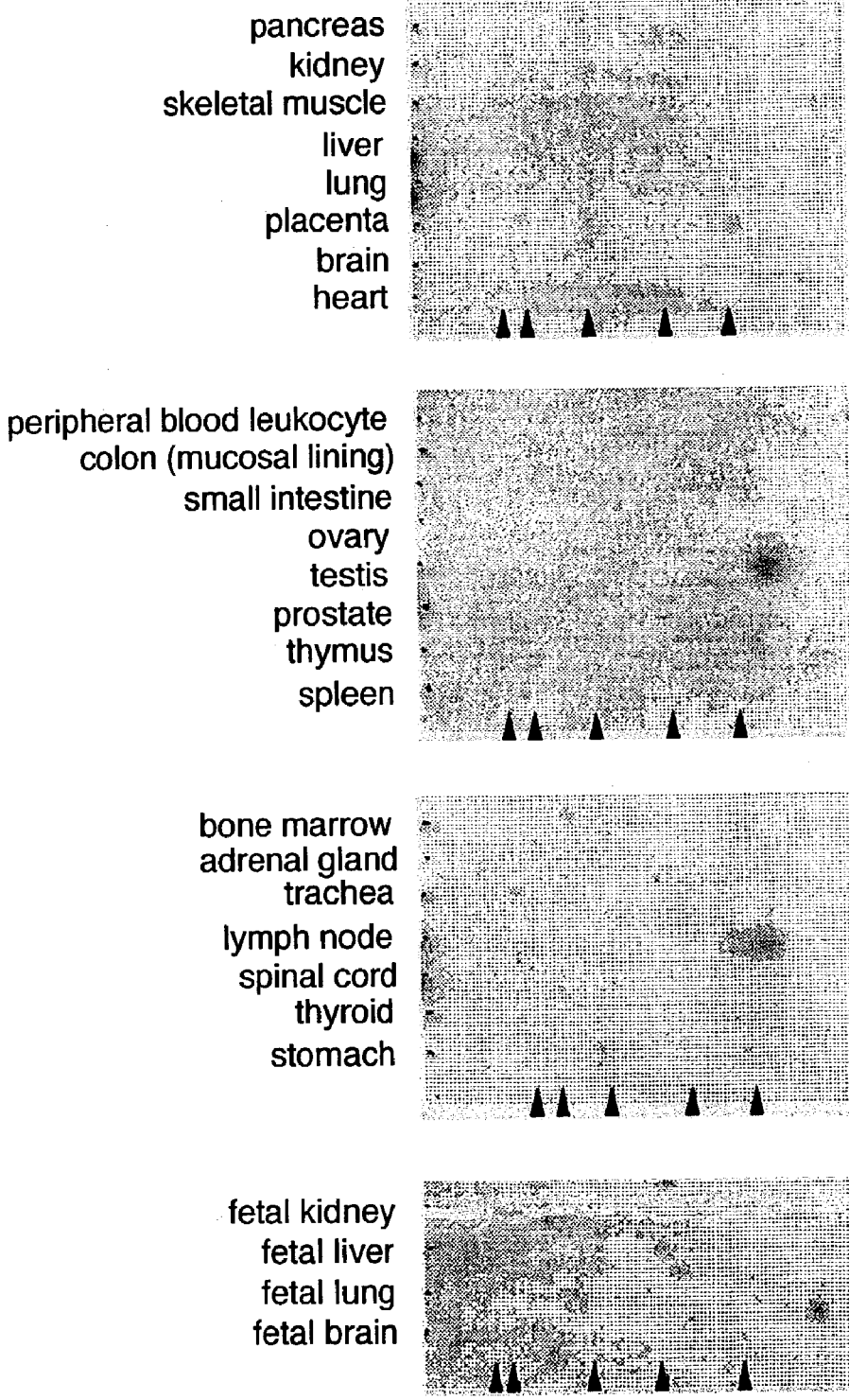
FIG. 4 shows the electrophoretic pattern of the "SGRF" expression in normal human tissue as detected by Northern blot analysis. Markers are, from the left, 9.5 kb, 7.5 kb, 4.4 kb, 2.4 kb, and 1.35 kb.

As a result, the full length of the isolated cDNA was 1 Kb, and encoded a protein comprising 189 amino acids (FIG. 1). This protein, not only had a consensus sequence typical of IL-6/G-CSF/MGF family (FIG. 2), but also a hydrophobic region considered to be a signal peptide in the N terminal (FIG. 3). Also, the binding site of N-type sugar-chain was not seen. In the 3' non-coding region, four mRNA destabilizing sequences called ARE (AT Rich element), often seen in cytokine mRNAs (FIG. 1), were detected, having characteristics of a typical cytokine. Based on the structural homology, this molecule was named "SGRF" (Interleukin-Six, G-CSF Related Factor).

EXAMPLE 2

Northern Blot Analysis of "SGRF" Expression

A 500 bp fragment obtained by treating pT7Blue-ILX1–4 with BamHI was used as the probe of "SGRF". The above probe was "☐-32P"dCTP labeled by random priming method using Ready-to Go DNA labeling beads (Pharmacia), and hybridization was done according to methods recommended by the Manufacturer within the ExpressHyb Hybridization Solution (Clontech) against the Multiple Tissue Northern Blot (Human, Human III, Human IV, Human Fetal II, Human Cancer Cell Line (Clontech) filters. As a result, in normal tissues, "SGRF" was mainly expressed in the testis and lymph nodes, and an mRNA of approximately 1 kb was detected. An extremely low expression was found in the thymus. However, since a long autoradiography (1 week) was required for the detection of these bands, the expression level in these are considered to be low. "SGRF" mRNA was not in a detectable level in other tissues.

Figure 5:
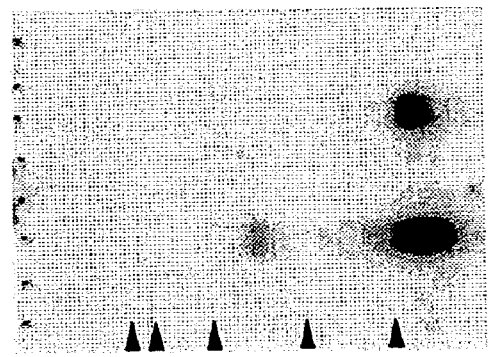
FIG. 5 shows the electrophoretic pattern of the "SGRF" expression in human fetal tissue and tumor cells as detected by Northern blot analysis. Markers are, from the left, 9.5 kb, 7.5 kb, 4.4 kb, 2.4 kb, and 1.35 kb.

When cancer cell lines were analyzed, very strong levels of expression were detected in two cell lines; K562 (Chronic Myelogenous Leukemia) and SW480 (Colorectal Adenocarcinoma) (FIG. 5). In the other cell lines, "SGRF" mRNA was not in a detectable level.

EXAMPLE 3

Construction of the "SGRF" Expression Vector

Two primers, "ILXATG" TTGAATTCCACCAT-GCTGGGGAGCAGAGCTGT/SEQ ID NO:14), "ILX-TAA" (AAAGATCTTAGGGACTCAGGGTTGCTGC/SEQ ID NO:15), were constructed, a gene consisting all the coding regions reconstituted by pT7Blue-1 LX 1–4 and pT7Blue-ILX5', and introduced into an animal cell expression vector. Namely, the band amplified using pT7Blue-ILX5'as the template and "ILX-2" and "ILXATG" as primers, and the band amplified using pT7Blue-ILX1–4 as the template and "ILX-1" and "ILXTAA" as primers, were mixed in equal amounts, and re-amplification was done using this as the new template with the primers "ILXATG" and "ILXTAA". The resulting band was treated with restriction enzymes EcoRI and BamHI, and cloned into the EcoRT, Bgl II site of all animal cell expression plasmid pCOS1 to create pCOS-SGRF. TaKaRa ExTaq (Takara Shuzo) was used for DNA amplification for 20 cycles of 30 sec at 96° C., following 40 sec at 60° C., and following 1 min 20 sec at 72° C.

EXAMPLE 4

The Polyclonal Antibody Corresponding to "SGRF"

Two kinds of partial peptides of "SGRF" (GGSSPAW-TQCQQLSQ/24–38 position of the amino acid sequence of SEQ ID NO:1, GDGCDPQGLRDNSQF, 74–88 position of the amino acid sequence of SEQ ID NO:1) were chemically synthesized. Two rabbits were immunized with these, respectively, to obtain polyclonal antibodies (Sawady). The respective antibodies were affinity-purified using respective peptide columns. The following analyses were done using one of the antibodies against the peptide of SGRF (24–38 position of the amino acid sequence of SEQ ID NO:1).

Alkyl phosphatase-binding, mouse-anti-rabbit IgG antibody and alkyl phosphatase substrate were used for detection.

EXAMPLE 5

Genomic DNA of SGRF

The following sequences were prepared and used for the analysis of the promoter regions-5'non translating region, translating region, 3' non-translating region from the genomic DNA library.

| | (SEQ ID NO:3) |
|---|---|
| ILX-1 | 5'-GAGAAGAGGGAGATGAAGAAGACTAC-3' |
| | (SEQ ID NO:4) |
| ILX-2 | 5'-CTGAGTCCTTGGGGGTCACAGCCAT-3' |
| | (SEQ ID NO:5) |
| ILX-3 | 5'-GTGGGACCTGCATATGTTGAAAATT-3' |
| | (SEQ ID NO:6) |
| ILX-4 | 5'-CCCCAAATTTCCCTTCCCATCTAATA-3' |
| | (SEQ ID NO:7) |
| ILX-5 | 5'-CCCTACTGGGCCTCAGCCAACTCCT-3' |
| | (SEQ ID NO:8) |
| ILX-6 | 5'-GGAGCAGAGAAGGCTCCCCTGTGAA-3' |
| | (SEQ ID NO:9) |
| ILX-7 | 5'-GGGCAGAGATTCCAGGAGGACTGGT-3' |
| | (SEQ ID NO:10) |
| ILX-8 | 5'-CCAGTCCTGGTGGAATCTCTGCCCA-3' |
| | (SEQ ID NO:11) |
| ILX-9 | 5'-GAAGCTCTGCACACTGGCCTGGAGT-3' |
| | (SEQ ID NO:12) |
| ILX-10 | 5'-CACTCCAGGCCAGTGTGTGCAGAGCTT-3' |
| | (SEQ ID NO:13) |
| ILX-11 | 5'-CTGAAGGGCTATGGTGGAGAA-3' |
| | (SEQ ID NO:14) |
| ILX-ATG | 5'-TTGAATTCCACCATGCTGGGGAGCAGAGCTGT-3' |
| | (SEQ ID NO:15) |
| ILX-TAA | 5'-AAAGATCTTAGGGACTCAGGGTTGCTGC-3' |
| | (SEQ ID NO:16) |
| ILX-TAAECO | 5'-AAGAATTGTAGGGACTCAGGGTTGCTGC-3' |
| | (SEQ ID NO:17) |
| SGRFg5' | 5'-GGTTTAAATATTTGTTCTCCCTTACCCC-3' |
| | (SEQ ID NO:18) |
| SGRFg37 | 5'-TTCAGCTGCTTGGGAGGCTGAGGCAGG-3' |
| | (SEQ ID NO:19) |
| SGRFg5'-2 | 5'-AGGAATTCCACCAGGACTGGTGCAAGGCGCA-3' |
| | (SEQ ID NO:20) |
| SGRFg3'-2 | 5'GTCTCGAGAAAATATCATTCTCCACCATCGCCCT-3' |

Figure 8:
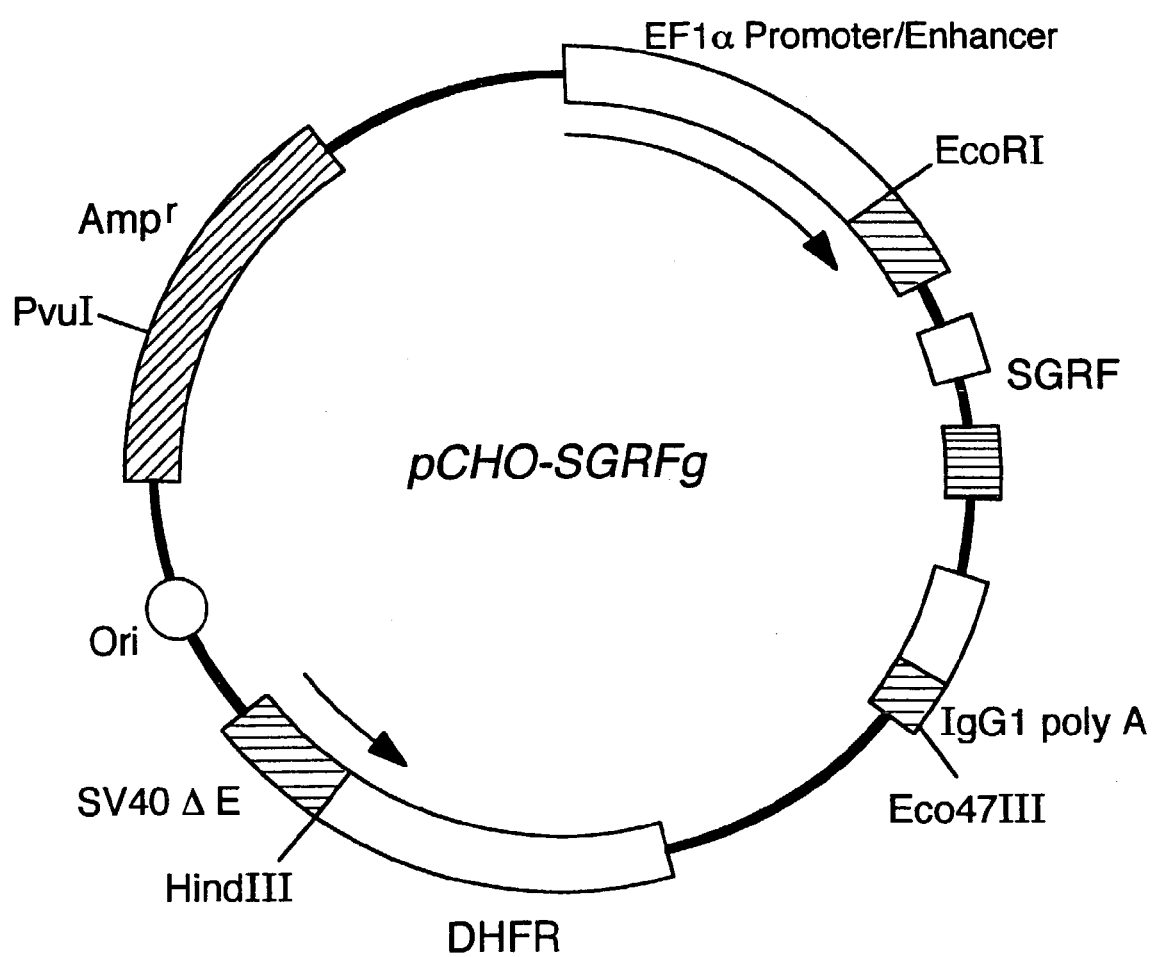
FIG. 8 shows the pCHO-SGRFg map.

Genomic DNA was amplified by PCR using, for the translation region, the above mentioned ILX-ATG primer and ILX-TAA primer and human genomic DNA (Clontech) as the template, resulting in a band amplified to approximately 1.5 kb. After treating this fragment with restriction enzymes EcoRI and BglII, cloning was done by inserting into the EcoRI-BamHI site of the CHO expression plasmid pCHO1. The nucleotide sequence or the vector obtained (pCHO-SGRFg) (FIG. 8) was analyzed using the primers described above. As a result, it was revealed to be the SGRF gene including 3 introns.

The amplifications of the 5' non-translating region containing the promoter, and the 3' non-translating region, were done using Genome Walker Kit as the template (Clontech), the attached AP1 and AP2 primers and the above-mentioned synthetic primers according to methods recommended by the Manufacturer.

First, for the 5' non-translating region, the $1^{st}$ PCR was done using Dra1 library as the template with AP1 and ILX-10 primers. Then, the $2^{nd}$ PCR was done with the AP2 and ILX-8 primers to obtain a band of approximately 400 bp.

For the 3' non-translating region, the $1^{st}$ PCR was done using PvuII library as the template with AP1 and ILX-5 primers, the $2^{nd}$ PCR with the AP2 and ILX-3 primers to obtain a band of app 800 bp.

The bands obtained were cut off from the agarose gel, and after purification, sequencing was done using 377 A DNA Sequencer (Perkin-Elmer). The genomic DNA sequence of SGRF (SEQ ID NO:21) is shown in FIG. 6 together with the deduced amino acids.

Figure 7:
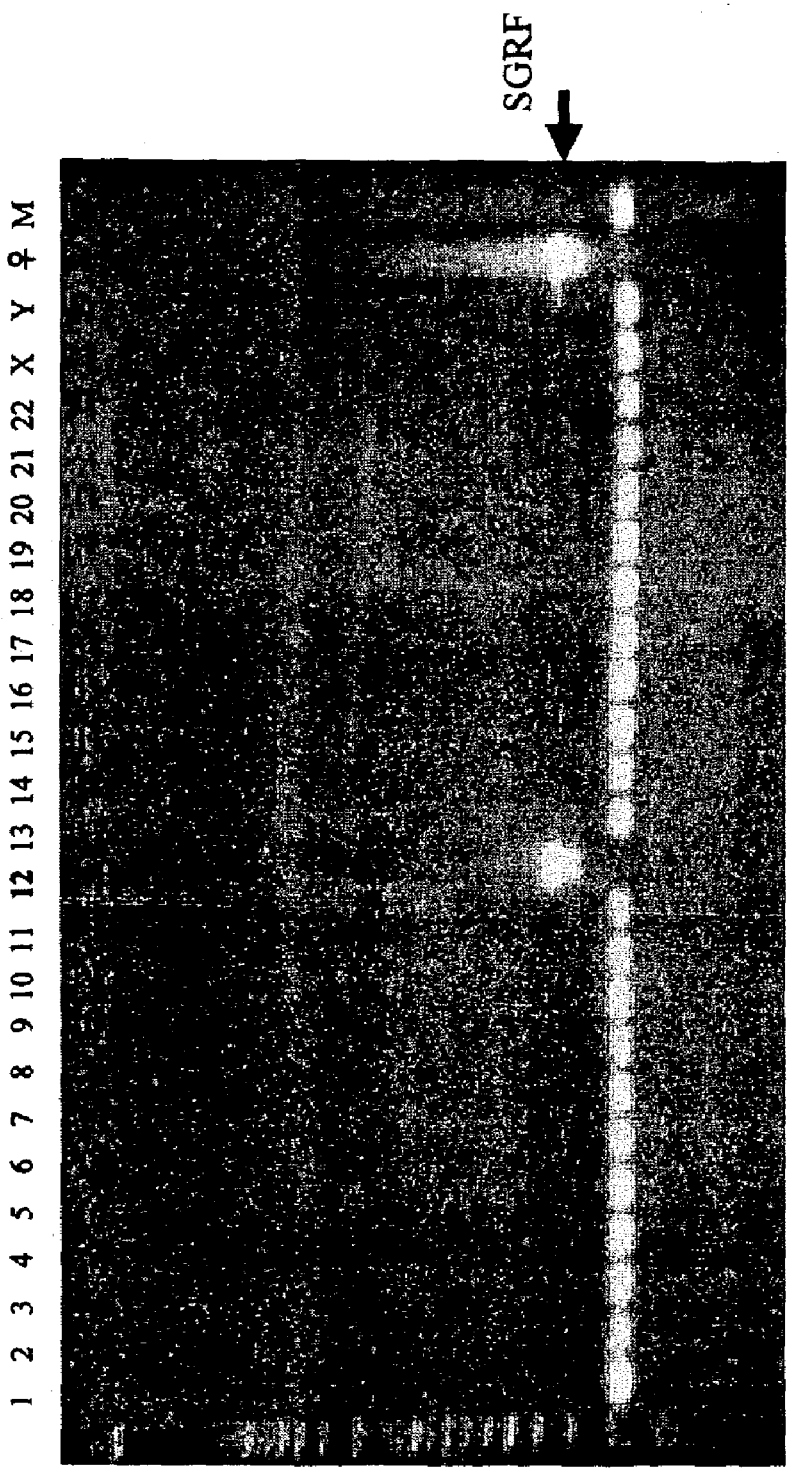
FIG. 7 shows the result of PCR analysis using NIGMS human/rodent somatic cell hybrid mapping panel #2. The numbers show the human chromosomes contained in the hybridoma DNA. ♀ shows human (female) genomic DNA, M shows mouse genomic DNA. 100 bp ladder has been used as a marker. The band seen around 200 bp is thought to be a non-specific background derived from mouse chromosomes.

Also, NIGMS human/rodent somatic cell hybrid mapping panel #2 and GeneBridge 4 Radiation Hybrid Panel (Research Genetics) were analyzed by PCR using ILX-1 and Ilx-6 primers to examine the chromosome location. As a result, from NIGMS human/rodent somatic cell hybrid mapping panel #2 analysis, it was revealed that the SGRF gene exists on the $12^{th}$ chromosome (FIG. 7).

The analysis from GeneBridge 4 Radiation Hybrid Panel, revealed that SGRF exists in 12q13 and is, Chromosome Chr12, Places 8.77 cR from WI-7107 (lod>3.0).

EXAMPLE 6

Establishment of a CHO Cell Line Expressing SGRF

Figure 9:
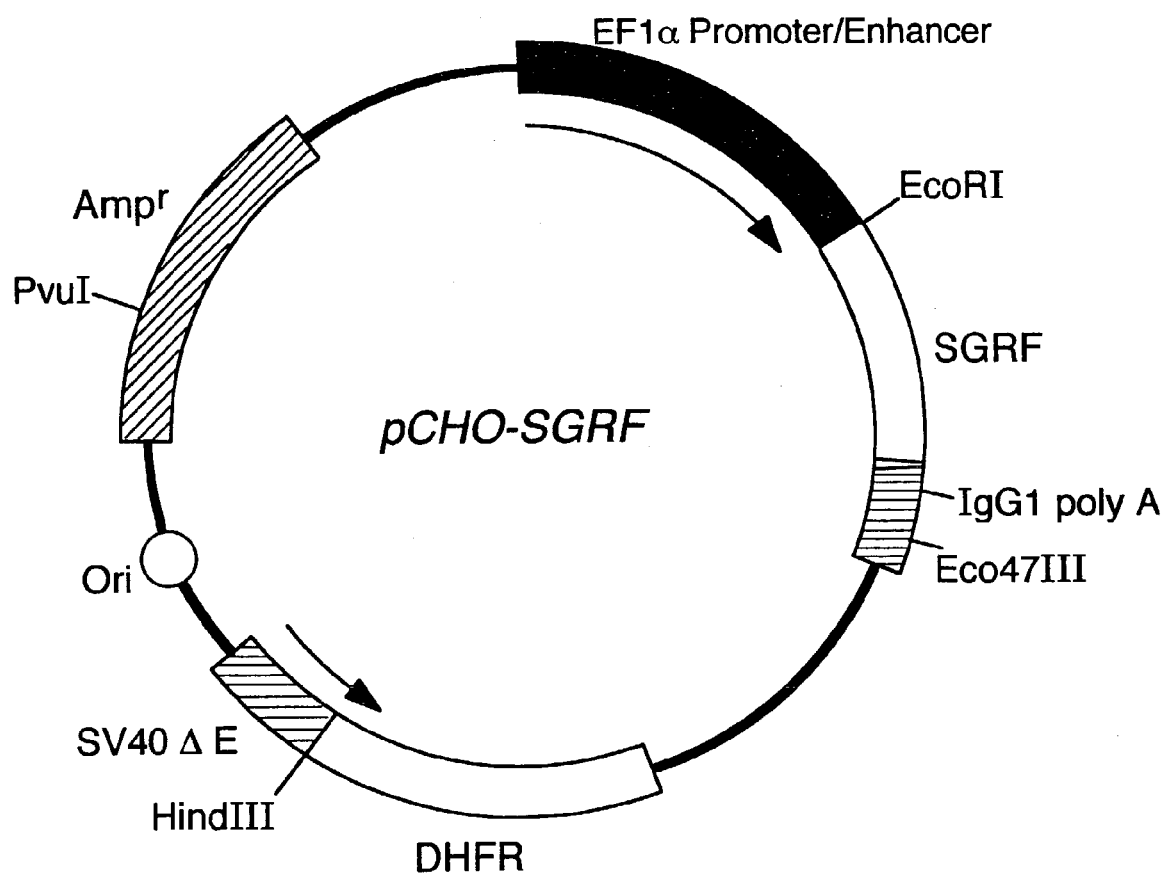
FIG. 9 shows the pCHO-SGRF map.

Similarly to pCOS-SGRF described in Example 3, DNA fragment of SGRF encoding region was prepared, was cloned to the EcoRI, BamHI site of the animal cell expression plasmid pCHO1 to create pCHO-SGRF (FIG. 9). PCHO-SGRF was then transfected into CHO cells by calcium phosphate method and gene-introduced cells were selected in alpha-MEM culture medium, which does not contain nucleotides. The culture supernatant was analyzed by SDS-PAGE and Western blotting using rabbit-polyclonal antibody.

As a result, a band with a molecular weight of about 20,000 was detected only in the culture supernatant of CHO cells having this vector.

Thereafter, the MTX concentration was increased sequentially to 20 nM, 100 nM and so on, and the gene was amplified while verifying the expression to establish a CHO cell strain, which constitutively secretes SGRF. This cell strain has been deposited in the depository institution given below.

(a) Name and address of the Depository Institution
  Name: National Institute of BioScience and Human-Technology Agency of Industrial Science and Technology
  Address: 1-3,Higashi-1-chome, Tsukaba-shi, Ibaraki 305-8566, Japan.
(b) Date of deposit (date of original deposit): Apr. 9, 1999.
(c) Accession Number: FERM BP-6699

EXAMPLE 7

Purification of SGRF

In order to review purification of SGRF, producing cells (CHO-SGRF 16-5 strain) proliferated to a confluent state, were rinsed with PBS, the medium was changed to a serum-free culture medium ASF104 (AJINOMOTO), cultured for 3 to 4 clays, and the culture supernatant was collected after filtering.

A 30 ml column was prepared using Phenyl-Sepharose HP (Amersham Pharmacia Biotech), equilibrated by 10 mM Tris pH 7.5, 100 mM NaCl, and the culture supernatant of the above mentioned CHO-SGRF16-5 strain cultured in ASF medium, was 1.5 times diluted using 10 mM Tris pH 7.5 and applied onto the column. After washing well with the equilibrating buffer, extraction was done with the same buffer containing 0.1% Tween 20. The extracted solution was applied to a DEAE-Sepharose FF column equilibrated with 10 mM Tris pH 7.5, 100 mM NaCl, washed well with the equilibrating buffer, and extracted using 10 mM Tris pH 7.5, 300 mM NaCl, recovering most of the SGRF. The extracted sample was according to normal methods by SDS-PAGE analysis, Western blot analysis as a crudely purified product. As a result, a band binding to the polyclonal antibody was detected at the site of a molecular weight of around 20,000 which was concentrated enough lo be detected by Silver-staining and Coomassie-staining.

This crudely purified SRF protein was blotted onto a PVDF membrane, stained with Coomassie blue, and a band with a molecular weight of about 20,000 was cut off to determine the N-terminal amino acid sequence using Model 492 protein sequencer (Applied Biosystems). As a result, the sequence was found to be X-Ala-Val-Pro-Gly-Gly-Ser. This matched the SGRF sequence of 20th Arg from the N-terminal to the 29th Ser, and the signal peptide was found to be cleaved between the 19th GLY and the 20th Arg.

From the above results, the mature protein of SGRF was calculated to be having 170 amino acids with a presumed molecular weight of 18,676 and an expected isoelectric point of 5.84.

EXAMPLE 8

SGFR Vector for the Creation of a Transgenic Mouse

Figure 10:
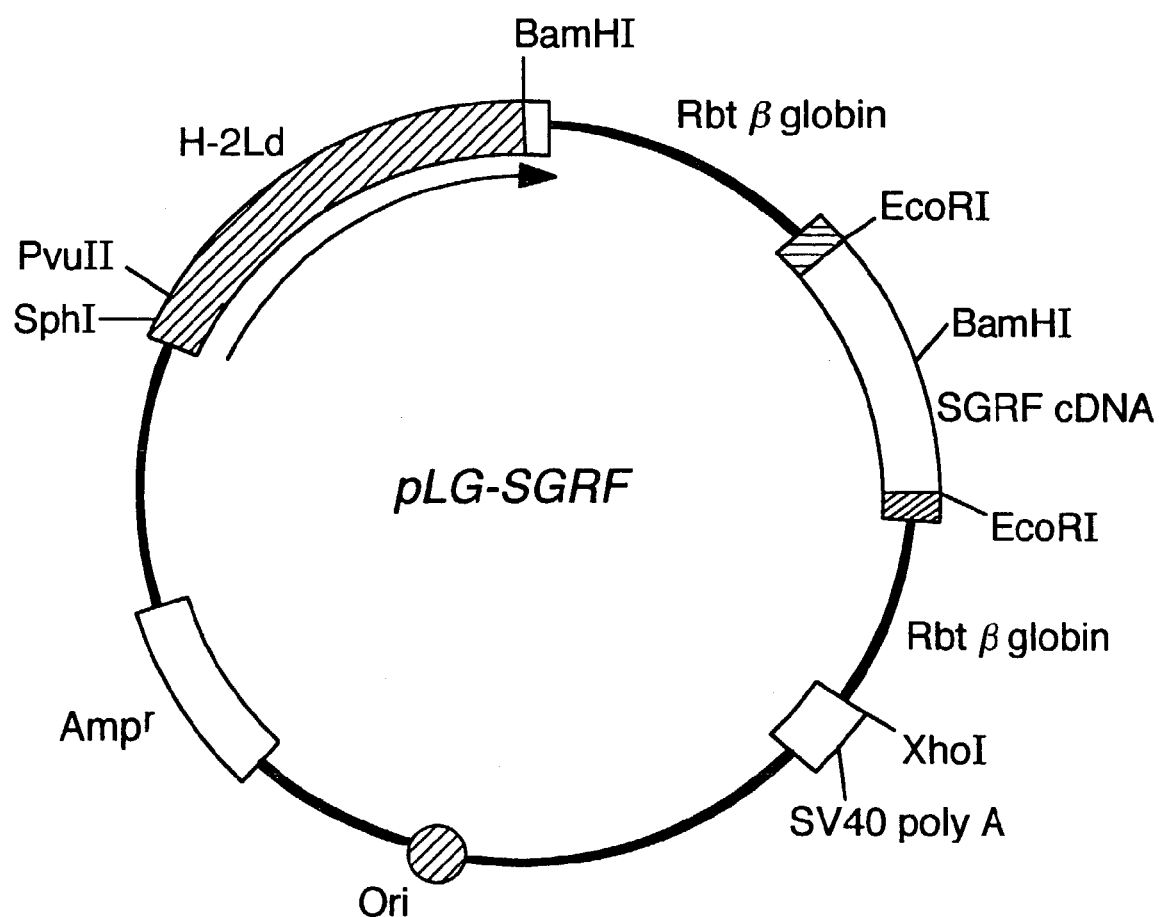
FIG. 10 shows the pLG-SGRF map.

SGRF cDNA was amplified from pCHO-SGRF using the primers ILX-ATG and ILX-TAAECO, cleaved with the restriction enzyme EcoRI, then inserted into the EcoRI site of transgenic expression plasmid pLG1 to create pLG-SGRF (FIG. 10).

Also, the region containing SGRF genomic DNA was amplified from human genomic DNA(clontech) using primers SGRF-5'_2 and SGRF-3'_2, treated with the restriction enzyme EcoRI, and then inserted into the EcoRI-XhoI site of the plasmid pLG1 to create pLG-SGRFg (FIG. 11).

EXAMPLE 9

Production of the Monoclonal Antibody

Five 8-week male Balb/c mice are immunized 2 mg/head with aluminum hydroxide gel as the adjuvant, and 20 μg/head of the above mentioned SGRF protein or the partial peptide as the antigen by injection into the peritoneal cavity. Re-immunization is done six times in every 2 weeks by injecting 20 μg/head of the above mentioned SGRF protein or the partial peptide. After the $3^{rd}$ immunization, blood is drawn from the eye-ground venous plexus and anti SGRF antibody titer in the serum is examined.

Three days after the final immunization, spleen cells are prepared from mice, and used for cell fusion. 1×108 splenocytes from the immunized mice washed well with MEM (Nissui Pharmaceuticals), and murine myeloma P3-U 1×108 are mixed and centrifuged for 5 min at 1000 rpm. 2 g Polyethylene glycol-1500 (PEG-1500), and 2 ml MEM are added while mixing well at 37° C. and centrifuged after 1 min at 600 rpm for 5 min. Further, 5 ml HBSS solution and 5 ml 20% FBS/MEM solution are added calmly, cells are suspended well, and centrifuged at 1000 rpm after 1 min, and the culture supernatant is discarded. The cells are re-suspended by adding 5 ml HAT medium (10-4M hypoxanthine, 4×10-7M aminopterin, and 1.5×10-5M thymidine supplemented medium). The cell suspension is seeded in 1ml/well into a 24-well culture plate (Nunc), and cultivated for 24 hr in a $CO_2$ incubator at 37° C., 5% $CO_2$, 95% air. 1 mil/well HAT medium is added and cultured further for another 24 hr. Then, 1 ml of culture supernatant is discarded, 1ml HAT medium is newly added and cultivated further for another 12 days.

For those wells in which colonized fusion cells can be detected, 1 ml culture supernatant is discarded, 1 ml HAT medium (aminopterin-excluded, above-mentioned HAT medium) added and cultured at 37° C. Exchange of the HAT medium is similarly done for the next two days and after culturing for 4 days, a portion of the culture supernatant is collected to measure the anti-SGPF antibody titer by ELISA.

For wells in which the antibody titer was detected, cloning is performed by limiting dilution twice more, and clones for which a stable antibody titer was detected, are selected as hybridomas producing anti-SGRF monoclonal antibody.

EXAMPLE 10

ELISA Method

50 μl/well of SGRF protein solution or the partial peptide solution is seeded into a 96-well culture plate (Immunoplate, Nunc) and is left to stand at room temperature for 2 hours to coat the antigen onto the bottom of the plate-well. Then, 200 μl/well of 10% FCS/PBS is added and left to stand at room temperature for 30 min. The above-mentioned plate is washed 3 times with PBS, serially diluted test sample (mouse serum, hybridomas culture supernatant, monoclonal antibody and such) is seeded in 50 μl/well, and left to stand at room temperature for 2 hours. Then, the plate is washed 3 times with PBS, and 100 times-diluted peroxidase-binding goat-anti-mouse IgG antibody is seeded in 50 μl/well as the secondary antigen and left to stand at room temperature for 2 hours. After washing with PBS, 200 μl/well of peroxidase substrate (1% hydrogen peroxide, 0.1M acetic acicl-0.05M phosphate buffer, 2 mM 2,2'-azino-di-3-ethyl-benzothiazine sulfate) is added and after leaving at room temperature for 10 to 30 min, the antibody titer is calculated using calorimetry at 414 nm.

EXAMPLE 11

Bone marrow cells were prepared by extracting the thighbone and shank-bone of 8 to 15 week C57BL/6 male mice (CLEAR JAPAN). After suspending in Nycodenz (Nycomed Pharm AS), the specific gravity was adjusted to 1.063, stratified to NycoPrep 1.077 Animal (Nycomed Pharm AS) and centrifuged for 30 min at 2300 rpm (Hitachi, 05PR22), 20° C. The intermediate layer was collected, suspended in FACS buffer (2% fetal Bovine Serum (FBS, Moregate) containing Dulbecco's phosphate buffer), was collected by centrifuging for 10 min at 1500 rpm, after which 1 μg of biotin-labeled anti-Mac-1 antibody, biotin-labeled anti-Gr-1 antibody, biotin-labeled anti-TER119 antibody, biotin-labeled anti-CD3ε antibody, and biotin-labeled B220 antibody (all by Pharmingen) were added per 1×106 cells. After leaving aside for 30 min on ice, was washed with FACS buffer, 1 μl avidin-labeled microbeads (10 Beads Avidin, ImmunoTech) were added and left to stand for 15 min on ice. Beads were then excluded by a magnetic holder, the floating cells were collected by centrifuging for 1 min (Tomy MRX-150) at 5000 rpm. After discarding the supernatant, 1 μg per 1×106 cells of FITC-labeled anti-CD34 antibody, PE-labeled anti Sca-1 antibody, APC-labeled c-kit antibody (all 3 by Pharmingen), RED613-labeled streptavidin (LifeTech Oriental) were added and reacted for 30 min on ice. After washing with FACS buffer, was suspended in 1 ml FACS buffer for 1×10$^6$ cells, and fractionated by EPICS ELITE (Beckman Coulter). The definitions of the respective fractions are as follows:
RED613-negative PE-negative APC-positive
=Lin(−) Sca-1(−) c-kit(+) fraction
RED613-negative PE-positive APC-positive
=Lin(−) Sca-1(+) c-kit(+)fraction
RED613-negative PE-positive APC-positive FITC-positive
=Lin(−) Sca-1(−) c-kit(+) CD34(+) fraction
RED613-negative PE-positive APC-positive FITC-negative
=Lin(−) Sca-1(+) c-kit(+) CD34(−) fraction The obtained cell fractions were diluted by the Iscove's modified Dulbecco's medium (10% FBS/IMDM) so that there were 10,000, 2000, and 400 cells per 1 ml of medium and were seeded in 50 ml into a 96-well culture plate.

To this, 50 μl of, (1) medium only (10% FBS/IMDM), (2) medium to which mock has been diluted to 20% (mock), (3) SGRF-expressed CHO culture supernatant (SGRF), (4) medium to which mouse kit ligand 10 ng/ml has been added (KL), (5) medium to which 20% mock, 10 ng/ml mouse kit ligand have been added (mock +KL), (6) SGRF-expressed CHO culture supernatant to which 10 ng/ml mouse kit ligand has been added (SGRF+KL), (7) medium to which 10 ng/ml mouse kit ligand, 5 ug/ml IL-11 has been added (KL+IL-11, were supplemented and then cultured for 10 days at 37° C., 5% CO$_2$.

Also, as for (1) and (3) mentioned above, 10 ng/ml, 1 ng/ml mouse kit ligand IL-11 were added respectively to prepare a similarly cultured lot as well (medium/expand, mock/expand, SGRF/expand, respectively).

Figure 12:
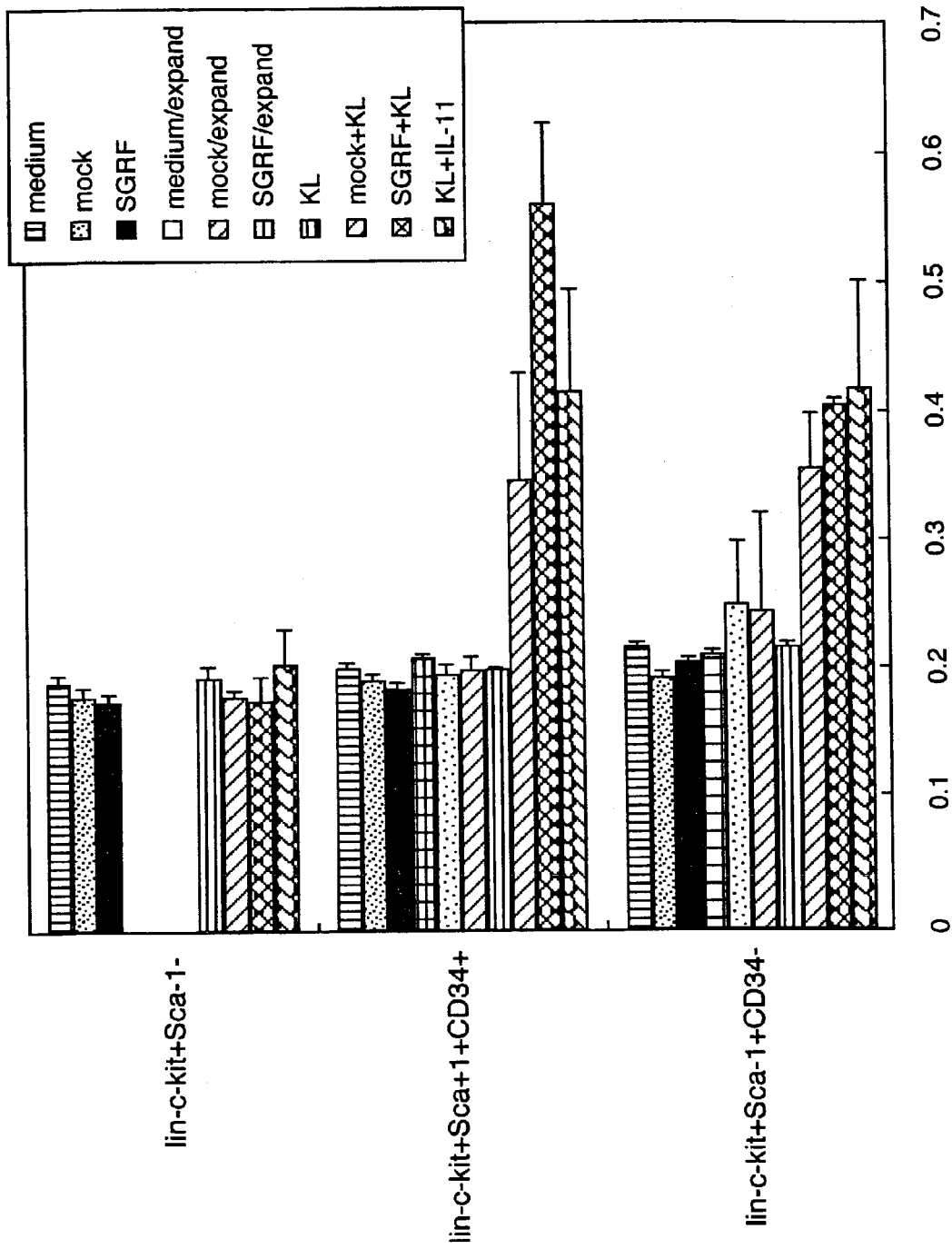
FIG. 12 shows the effect of the SGRF-gene-inserted, CHO cell culture supernatant on the proliferation of bone marrow cells.

After completion of culture, cell number was detected using a Cell proliferation Assay Kit (Promega) as measured by Microplate Reader Model 3550 (Bio-Rad) for the absorbance at 490 nm (FIG. 12).

As a result, although SGRF-alone showed no proliferation supporting activity towards Lin negative, Sca-1 positive and c-kit positive cells, such a proliferation supporting activity was shown under the presence of the mouse kit ligand. This activity was stronger in CD34 positive cells. Also, if the mouse kit ligand did not exist at the initial stages of culture, cells did not proliferate even when the ligand was supplemented afterwards. From this fact it can be assumed that SGRF does not have an activity to support stem cells.

Industrial Applicability

The present invention provided a novel cytokine-like protein and the DNA encoding the protein. Furthermore, a vector into which the DNA is inserted, a transformant possessing said DNA and the methods of production of a recombinant protein are provided. A compound that binds to the protein and a screening method for a compound that regulates its activity are also provided.

Since the protein of the invention and the gene, alike other cytokines, are believed to be associated with the activity or cell proliferation and differentiation of cells of the immune and hematopoietic systems, the use of a compound that controls said protein is anticipated in diseases relating to the immune or hematopoietic systems and defects in cell proliferation. A number of embodiments of the invention have been described. Nevertheless, it will be understood that various modifications may be made without departing from the spirit and scope of the invention.

What is claimed is:

1. An isolated nucleic acid comprising a sequence encoding a polypeptide comprising the amino acid sequence of SEQ ID NO: 1.

2. A vector comprising the nucleic acid of claim 1.

3. A cultured host cell comprising the nucleic acid of claim 1.

4. A method of producing a polypeptide comprising the amino acid sequence of SEQ ID NO: 1, the method comprising culturing the cultured host cell of claim 2 in a culture, expressing the polypeptide in the cultured host cell, and isolating the polypeptide from the culture.

5. The nucleic acid of claim 1, wherein the polypeptide consists of the amino acid sequence of SEQ ID NO: 1.

6. A vector comprising the nucleic acid of claim 5.

7. A cultured host cell comprising the nucleic acid of claim 5.

8. A method of producing a polypeptide consisting of the amino acid sequence of SEQ ID NO: 1, the method comprising culturing the cultured host cell of claim 7 in a culture, expressing the polypeptide in the cultured host cell, and isolating the polypeptide from the culture.

* * * * *

UNITED STATES PATENT AND TRADEMARK OFFICE
CERTIFICATE OF CORRECTION

PATENT NO. : 7,252,967 B2  
APPLICATION NO. : 10/440066  
DATED : August 7, 2007  
INVENTOR(S) : Yuichi Hirata Page 1 of 1

It is certified that error appears in the above-identified patent and that said Letters Patent is hereby corrected as shown below:

In the Abstract:

Line 4: delete "printers" and insert --primers--

Column 47, line 51:

Delete "claim 2" and insert --claim 3--

Signed and Sealed this

Ninth Day of June, 2009

JOHN DOLL  
*Acting Director of the United States Patent and Trademark Office*